United States Patent [19]

Kohmura et al.

[11] Patent Number: 5,672,193
[45] Date of Patent: Sep. 30, 1997

[54] PRODUCTION APPARATUS FOR PRODUCING AN OPTICAL FIBER CABLE

[75] Inventors: Yukio Kohmura, Chiba; Yoshinori Ishida, Ichihara; Takashi Hibino, Urawa, all of Japan

[73] Assignee: The Furukawa Electric Co., Ltd., Tokyo, Japan

[21] Appl. No.: 558,224

[22] Filed: Nov. 17, 1995

Related U.S. Application Data

[63] Continuation of Ser. No. 390,817, Feb. 16, 1994, abandoned, which is a continuation of Ser. No. 120,740, Sep. 14, 1993, abandoned, which is a division of Ser. No. 707,744, May 30, 1991, Pat. No. 5,262,726.

[30] Foreign Application Priority Data

| May 30, 1990 | [JP] | Japan | 2-140332 |
| Apr. 12, 1991 | [JP] | Japan | 3-108733 |
| Apr. 12, 1991 | [JP] | Japan | 3-108734 |

[51] Int. Cl.$^6$ .................................. C03B 37/023
[52] U.S. Cl. ................... 65/484; 65/491; 65/529; 324/230; 324/232
[58] Field of Search .................. 324/230, 232; 65/382, 484, 491, 529, 425, 423

[56] References Cited

U.S. PATENT DOCUMENTS

| 3,229,196 | 1/1966 | Neale | 324/230 |
| 4,530,750 | 7/1985 | Aisenberg | 65/3.12 |
| 4,556,845 | 12/1985 | Strope et al. | 324/230 |
| 4,752,739 | 6/1988 | Wang | 324/230 |
| 4,893,079 | 1/1990 | Kustra | 324/230 |
| 5,017,869 | 5/1991 | Oliver | 324/230 |
| 5,021,072 | 6/1991 | Atkins | 65/3.11 |
| 5,062,298 | 11/1991 | Falcoff | 324/230 |
| 5,086,274 | 2/1992 | Gobin | 324/230 |
| 5,142,228 | 8/1992 | Kingsbury | 324/230 |
| 5,180,978 | 1/1993 | Postma | 324/232 |
| 5,191,286 | 3/1993 | Fischer | 324/230 |
| 5,237,271 | 8/1993 | Hedengren | 324/232 |
| 5,262,726 | 11/1993 | Kohmura | 324/232 |

OTHER PUBLICATIONS

IEEE Standard Dictionary . . . , Jay, F, 1984, p. 519 IEEE, NY.
Encyclopedia of Electronics, Gibilisco, S. p. 522 1985, Tab Books Inc, PA. Blue Ridge Summit.
Van Nostrand's Scientific Encyclopedia, 1982, p. 1805 Sixth edition.

*Primary Examiner*—John Hoffmann
*Attorney, Agent, or Firm*—Staas & Halsey

[57] ABSTRACT

An apparatus for accurately inspecting an electroconductive film using an eddy current and an apparatus for production of an optical fiber which measures on-line the electrical resistance, which shows the state of formation of the electroconductive hermetic coating of the optical fiber by an electroconductive film inspection method and reflects back the measurement results to the hermetic coating forming conditions. Optical fiber is made up of a core, a cladding, amorphous carbon film or other electroconductive hermetic coating formed on the outer surface of the cladding, and a protective coating. The electrical resistance of the hermetic coating generates an eddy current at the coating, the eddy current generated is detected, and the phase angle of the complex impedance is detected to enable calculation. In particular, to accurately detect the phase angle, the high frequency current for generating the eddy current is changed by a low frequency of about 1/100th of the high frequency to change the average intensity and obtain at least two points of measurement defining the above phase angle. The electrical resistance of the hermetic coating is calculated from this phase angle. The electrical resistance shows the state of formation of the hermetic coating. The measurement value of the electrical resistance of the hermetic coating is used for setting the hermetic coating production conditions. The electroconductive film inspection method of the present invention may also be used for quality control etc. of thin films.

11 Claims, 14 Drawing Sheets

PRODUCTION APPARATUS FOR PRODUCING AN OPTICAL FIBER CABLE

This application is a continuation of application Ser. No. 08/390,817, filed Feb. 16, 1994, now abandoned, which is a continuation of application Ser. No. 08/120,740, filed Sep. 14, 1993, now abandoned, which is a divisional of application Ser. No. 07/707,744, filed on May 30, 1991, now U.S. Pat. No. 5,262,726.

BACKGROUND OF THE INVENTION

1. Field of the Invention

The present invention relates to a method and system (apparatus) for inspection of electroconductive film which uses an eddy current to inspect electroconductive hermetic coating formed on the outer surface of the cladding of optical fiber, magnetic film, and other electroconductive film on-line by a nondestructive system and a process and system for production of a hermetically coated optical fiber using the electroconductive film inspection method.

2. Description of the Related Art

In general, an optical fiber is comprised of an optical fiber line made of a core spun from a quartz optical fiber preform and a cladding on whose surface there is provided a protective plastic coating.

In such an optical fiber with a plastic coating, the invasion of hydrogen or moisture in the atmosphere into the core causes an increase in the signal transmission loss of the core along with the passage of time.

To eliminate this defect of optical fibers, there has been proposed a hermetically coated optical fiber with the surface of the optical fiber line comprised of the core and cladding, that is, the outer surface of the cladding, having a hermetic coating comprised of an inorganic substance, such as amorphous carbon, formed on it to prevent penetration of atoms of hydrogen or moisture to the core portion.

A hermetically coated optical fiber of this structure has the effect of preventing penetration and invasion of hydrogen and moisture to the core portion of the optical fiber line, due to the feature of having the above-mentioned hermetic coating, and will not suffer from an increase in the optical signal transmission loss over long periods of time and further will mechanically protect the outer surface of the optical fiber and increase the mechanical strength of the optical fiber.

In such a hermetically coated optical fiber, the stability of the state of formation of the hermetic coating in the longitudinal direction of the optical fiber is important. If there is a variation in the quality or the thickness at even one location, atoms of hydrogen and moisture will invade the core portion from there and invite an increase in the signal transmission loss. Therefore, it is necessary to ensure that the hermetic coating is provided uniformly over the entire length of the optical fiber.

An amorphous carbon hermetic coating usually has a thickness of 500 to 1000 Å and is a conductor having an electrical resistance of several to several tens of kilohms/cm. Therefore, as the method for evaluating the state of formation of the hermetic coating, it is effective to measure the electrical resistance.

As a conventionally known method for evaluating the state of formation of a hermetic coating, there is known the method of removing the plastic coating formed on the outer surface of the optical fiber and measuring off-line the electrical resistance of the peeled off hermetic coating using a tester. This electrical resistance measurement method, however, inspects a portion of the optical fiber and therefore has the problem that it cannot inspect the state of formation of the hermetic coating continuously over the entire length in the longitudinal direction of the optical fiber. Further, the above-mentioned electrical resistance measurement method removes the plastic coating, so the optical fiber at the position examined is wasted and thus it is further impossible to inspect the entire optical fiber. Further, the conventional electrical resistance measurement method had the problem of a low efficiency of measurement work due to it being performed manually.

It would be desirable to feed back the results of measurement of the electrical resistance to the production conditions in the process of formation of the hermetic coating and to prevent in advance the formation of defective hermetic coatings. In the above-mentioned electrical resistance inspection method, however, it is impossible to feed back the results of the inspection on-line to the production conditions and therefore it is impossible to achieve the above-mentioned object.

As another conventional method, consideration has been given to a contact type electrical resistance measurement system wherein an electrical resistance measurement probe is brought into direct contact with the hermetic coating before the application of the plastic coating, but if a probe etc. is brought into direct contact with the hermetic coating, it sometimes causes scratches on the hermetic coating and a reduction of strength of the optical fiber, so this method cannot be used.

Therefore, it is necessary to measure the electrical resistance of the hermetic coating in a noncontact state after the application of the plastic coating. As one method for this, it has been attempted to measure the electrical resistance of the hermetic coating using the eddy current inspection method.

The eddy current inspection method is based on the principle of measuring the electrical resistance of the hermetic coating using the fact that when a conductor is placed in an alternating magnetic field, an eddy current flows in the conductor in a direction to cancel out the magnetic field and the magnitude and distribution of the eddy current change according to the shape of the conductor, the conductivity, the magnetic permeability, the internal defects, etc. That is, the eddy current inspection method is a method for determining the state of the inspected object, that is, the conductor, by using the fact that the magnetic field generated by an eddy current changes the impedance of a detection coil by mutual induction and detecting the changes in impedance as changes in the voltage and phase.

The conventional eddy current inspection method, however, is aimed at measuring the position and size of the defects of the inspected object and is a method which separates sharp changes in the output signal from noise by differentiating the signals, so cannot be applied to the present invention.

Further, there is already known the method for measuring the electrical resistance of a conductor from its eddy current by applying to an inspection coil an AC current of a plurality of superposed frequencies, but in this case signals of frequencies sensitive to defects and signals of frequencies not sensitive to them are processed to cancel out the effects of noise and discriminate the shapes of defects.

When measuring the electrical resistance for evaluating the state of formation of the hermetic coating of an optical fiber, as aimed at in the present invention, the object is to detect sharp changes in the electrical resistance of the hermetic coating, of course, and also continuous changes of the optical fiber in the longitudinal direction and stability is sought in the measurement apparatus. When an extremely highly sensitive measurement precision is demanded, however, in this way, in the prior art method the zero point of the output unavoidably drifts due to temperature. Even if the relative interval between the inspected object and the detection coil changes only slightly, the output value ends up changing and the problem arises of an inability to measure the object accurately.

FIG. 1 shows this situation. In the figure, the horizontal axis (X axis) shows the value of the real number portion of the complex impedance, while the vertical axis (Y axis) shows the imaginary number portion of the complex impedance. The phase angle shows the electrical resistance, but as shown in FIG. 1, when the measurement results fluctuate, it is impossible to accurately calculate the electrical resistance.

SUMMARY OF THE INVENTION

The object of the present invention is to provide an electroconductive film inspection method which can accurately measure the electrical resistance of a hermetic coating or other electroconductive film by a nondestructive system and an electroconductive film inspection system using this electroconductive film inspection method.

Another object of the present invention is to provide an electroconductive film inspection method which can measure continuously and on-line the electrical resistance of an electroconductive film and a system using that inspection method.

Still another object of the present invention is to provide an electroconductive film production process which produces an electroconductive film continuously with a high quality by using the above-mentioned electroconductive film inspection method to evaluate the state of formation of a hermetic coating or other electroconductive film and feeding back the results of the evaluation to the electroconductive film forming process.

According to a first aspect of the present invention, there is provided an electroconductive film inspection method comprising a step of changing an average intensity of a magnetic field of a frequency sufficiently high to generate an eddy current at an electroconductive film being inspected by a frequency sufficiently lower than the high frequency of the high frequency magnetic field and applying the high frequency magnetic field from near the electroconductive film to the electroconductive film to generate an eddy current at the electroconductive film; a step of detecting the eddy current generated at the electroconductive film; and a step of calculating an electrical resistance of the electroconductive film corresponding to a phase angle of a complex impedance vector based on the detected eddy current and there is provided an electroconductive film inspection system provided with an eddy current generation and detection sensor arranged near an electroconductive film to be inspected; a high frequency power source which generates a high frequency current of a frequency sufficiently high for generating an eddy current at the electroconductive film and which applies it to the eddy current generation and detection sensor; an average intensity changing means which applies the high frequency current from the high frequency power source to the eddy current generation and detection sensor while changing the average intensity thereof by a frequency sufficiently lower than the frequency of the high frequency current; and a means for calculating the electrical resistance of the electroconductive film from the eddy current detected by the eddy current generation and detection sensor.

According to a second aspect of the present invention, there is provided a production process for an optical fiber having a step of forming an optical fiber line having a core and a cladding; a step of forming an electroconductive hermetic coating on the surface of the cladding; a step of changing the average intensity of the high frequency magnetic field of a frequency sufficiently high for generating an eddy current close to the hermetic coating by a frequency sufficiently lower than the frequency of the high frequency magnetic field and of applying the changed magnetic field from near the hermetic coating to the hermetic coating; a step of detecting the eddy current generated at the hermetic coating; a step of calculating the electrical resistance of the hermetic coating corresponding to a phase angle of a complex impedance vector from the detected eddy current; and a step of adjusting the hermetic coating forming conditions at the hermetic coating forming step based on the calculated electrical resistance and there is provided a production system for an optical fiber having a drawing furnace for drawing an optical fiber material and forming an optical fiber line having a core and a cladding; a reaction furnace which is arranged after the drawing furnace, has introduced in it a hermetic coating forming material gas and the drawn optical fiber line, has a thermal decomposition reaction which precipitates the material gas on the surface of the cladding of the introduced optical fiber line, and thus forms an electroconductive hermetic coating; an eddy current generation and detection sensor arranged near the hermetic coating; a high frequency power source for generating a current which is applied to the eddy current generation and detection sensor and is of a frequency sufficiently high for generating an eddy current at the hermetic coating; an average intensity changing means for applying the high frequency current from the high frequency power source to the eddy current generation and detection sensor while changing the average intensity by a frequency sufficiently lower than the frequency of the high frequency current; a means for calculating the electrical resistance of the hermetic coating from the eddy current detected by the eddy current generation and detection sensor; and a control means for adjusting the hermetic coating forming conditions based on the electrical resistance from the electrical resistance calculating means.

According to a third aspect of the present invention, there is provided a method for adjustment of conditions for forming a hermetic coating of an optical fiber in a process for production of an optical fiber by forming an optical fiber line having a core and a cladding and forming an electroconductive hermetic coating on the surface of the cladding, the method having a step of changing the average intensity of a high frequency magnetic field of a frequency sufficiently high for generating an eddy current close to the hermetic coating by a frequency sufficiently lower than the frequency of the high frequency magnetic field and of applying the changed magnetic field from near the hermetic coating to the hermetic coating; a step of detecting the eddy current generated at the hermetic coating; a step of calculating the electrical resistance of the hermetic coating corresponding to a phase angle of a complex impedance vector from the detected eddy current; and a step of adjusting the hermetic coating forming conditions at the hermetic coating forming step based on the calculated electrical resistance and there is provided a system for adjustment of conditions for forming a hermetic coating of an optical fiber in a system for production of an optical fiber by drawing an optical fiber material and forming an optical fiber line having a core and a cladding and forming an electroconductive eddy current on the surface of the cladding of the optical fiber line, the system having an eddy current generation and detection sensor arranged near the hermetic coating; a high frequency power source for generating a current which is applied to the eddy current generation and detection sensor and is of a frequency sufficiently high for generating an eddy current at the hermetic coating; an average intensity changing means for applying the high frequency current from the high frequency power source to the eddy current generation and detection sensor while changing the average intensity by a frequency sufficiently lower than the frequency of the high frequency current; a means for calculating the electrical resistance of the hermetic coating from the eddy current detected by the eddy current generation and detection sensor; and a control means for adjusting the hermetic coating forming conditions based on the electrical resistance from the electrical resistance calculating means.

According to a fourth aspect of the present invention, there is provided an electroconductive film inspection method and system which inspect two-dimensionally an electroconductive film which is spread over a plane and evaluates the state of its formation. The principle of the inspection method is based on the above electroconductive film inspection method.

BRIEF DESCRIPTION OF THE DRAWINGS

The above-mentioned object and features of the present invention and other objects and features will become clearer by the detailed disclosure of the invention given in relation to the following appended drawings, in which.

DESCRIPTION OF THE PREFERRED EMBODIMENTS

Figure 2:
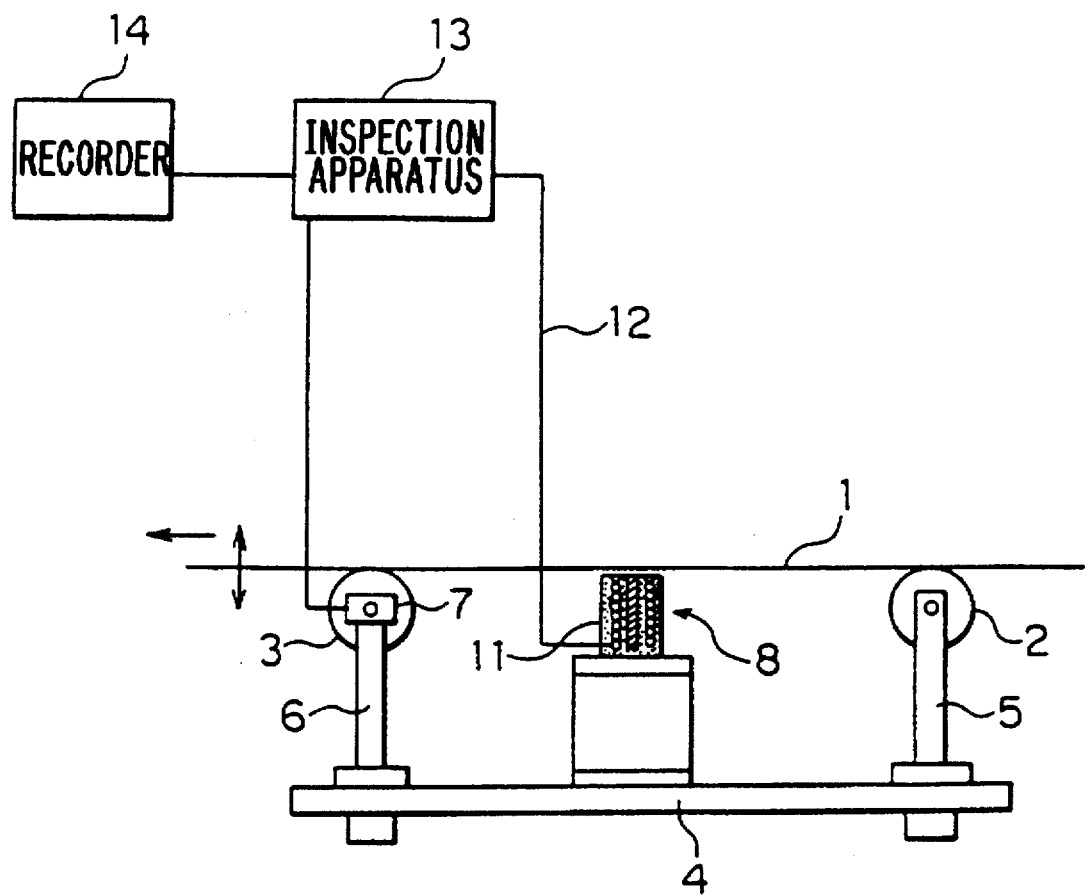
FIG. 2 is a constitutional view of a hermetic coating electrical resistance measurement system as a first embodiment of the electroconductive film inspection method of the present invention and an electroconductive film inspection system using the same.

FIG. 2 shows the constitution of a hermetic coating electrical resistance measurement system for measuring continuously and without contact the electrical resistance of a hermetic coating of a hermetically coated optical fiber using an eddy current, as a first embodiment of the electroconductive film inspection method and electroconductive film inspection system of the present invention.

The hermetic coating electrical resistance measurement system has first and second guide rollers 2 and 3 which run and guide a hermetically coated optical fiber 1, stands 5 and 6 which rotatably support the guide rollers 2 and 3, and a frame 4 which supports the stands 5 and 6. The second guide roller 3 is provided with a vibrator 7, which can vibrate the hermetically coated optical fiber 1 up and down while it is running. Near the running hermetically coated optical fiber 1 is disposed a probe type eddy current generation and inspection sensor (also referred to as an eddy current generation and detection sensor) 8.

Figure 3:
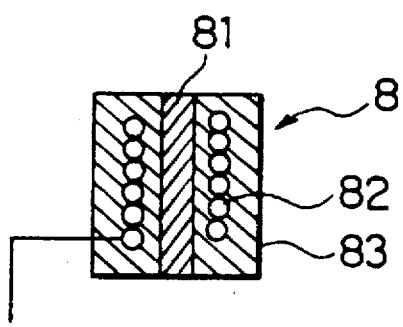
FIG. 3 is a sectional view of an eddy current generation and inspection sensor shown in FIG. 2.

The eddy current generation and inspection sensor 8, as shown enlarged in FIG. 3, is comprised of a magnetic core 81 at the outer periphery of which is laid the coil 82 in a coaxial state, all of which is molded to an integral body by a resin 83. This eddy current generation and inspection sensor 8 generates an eddy current near the hermetic coating 1c, shown in FIG. 4, and detects the eddy current generated. The dimensions of the eddy current generation and inspection sensor 8 used in this embodiment are shown in Table 1.

TABLE 1

| Inside diameter of coil 82 | 1.6 mm |
| Wire diameter of coil 82 | 0.05 mm |
| Number of turns of coil 82 | 100 to 150 |
| Length of coil 82 | 8 to 10 mm |

The hermetic coating electrical resistance measurement system further has an inspection apparatus 13 and a recorder 14. The inspection apparatus 13 has a power source which generates a high frequency current for generating the eddy current to the inspection apparatus 13 through the eddy current generation and inspection sensor 8 and has a processing unit, for example, a microcomputer, which calculates the electrical resistance of the hermetic coating 1c from the detected eddy current. The inspection apparatus 13 is connected through a cord 12 to the eddy current generation and inspection sensor 8. Further, the inspection apparatus 13 causes the vibrator 7 to vibrate at a predetermined frequency to vibrate the hermetically coated optical fiber 1 up and down. The frequency $f_1$ of the high frequency current for generating the eddy current which is applied to the eddy current generation and inspection sensor 8 in this embodiment and the vibration frequency of the vibrator 7 are shown in Table 2.

TABLE 2

| Frequency $f_1$ of eddy current generation current: | 1 to 3 MHz |
| Vibration frequency of vibrator 7 | 150 Hz |

Figure 4:
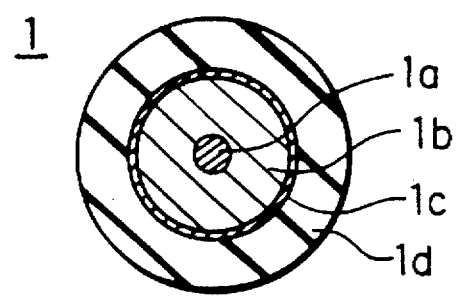
FIG. 4 is a sectional view of a hermetically coated optical fiber shown in FIG. 2.

A sectional view of the hermetically coated optical fiber 1 covered by the measurement is given in FIG. 4. This hermetically coated optical fiber 1 is an integrally molded optical fiber and comprises an optical fiber line made of a core 1a of a diameter of 10 microns and a cladding 1b of an outer diameter of 125 microns, a hermetic coating 1c of a thickness of 500 to 1000 Å formed on the outer surface of the cladding 1b, and a protective plastic coating 1d. The electrical resistance of the hermetic coating 1c is several kΩ/cm to several tens kΩ/cm.

The vibrator 7 is driven by a signal from the inspection apparatus 13 to forcibly vibrate the hermetically coated optical fiber 1 in a direction perpendicular to the direction of running of the hermetically coated optical fiber 1. By this, the hermetically coated optical fiber 1 and the eddy current generation and inspection sensor 8 approach and move apart from each other by the above vibration frequency.

When the hermetically coated optical fiber 1 is moved apart from the eddy current generation and inspection sensor 8, the complex impedance of the coil 82 becomes zero and when it is moved close, the complex impedance increases. The results of detection of the coil 82 are input by the inspection apparatus 13 and recorded in the recorder 14.

Figure 5:
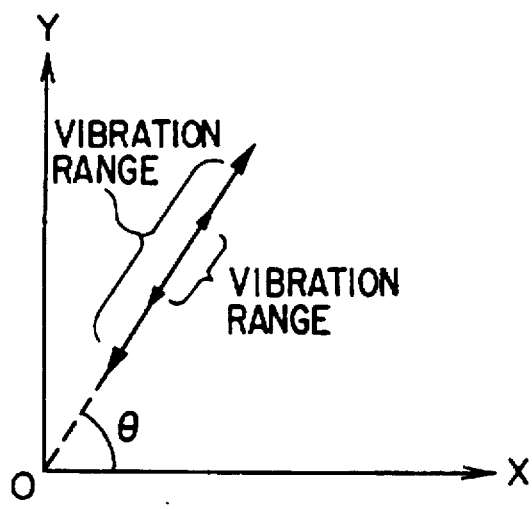
FIG. 5 is a characteristic graph showing the amplitude characteristic of a complex impedance measured in the hermetic coating electrical resistance measurement system of FIG. 2.
Figure 6:
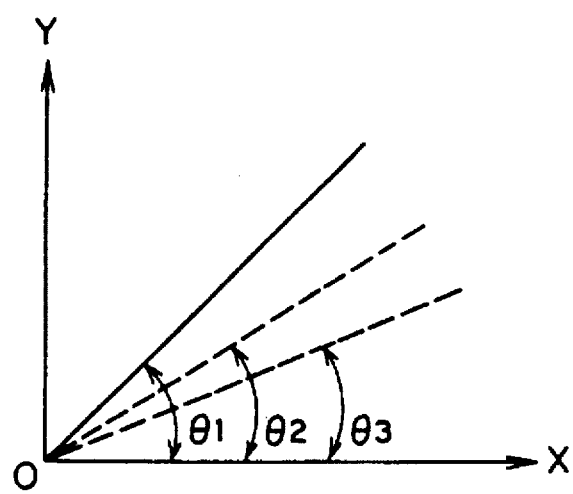
FIG. 6 is a characteristic graph showing the phase characteristic of the complex impedance measured in the electroconductive film inspection system of FIG. 2.

FIG. 5 shows the results of the plotting of the changes in the complex impedance by the recorder 14. The horizontal axis shows the real complex impedance, while the vertical axis shows the imaginary number. If the electrical resistance of the hermetic coating 1c is constant, then the phase angle θ is constant and the scope of change of the complex impedance vector changes in proportion to the magnitude of the vibration of the hermetically coated optical fiber 1. On the other hand, the phases $θ_1$ to $θ_3$ of the complex impedance changes, as shown in FIG. 6, according to the magnitude of the electrical resistance of the hermetic coating 1c. Therefore, if the phases θ are found, then it is possible to measure the electrical resistance of the hermetic coating 1c. The inspection apparatus 13 calculates the electrical resistance of the hermetic coating 1c from the measured phase angle θ.

When the complex impedance vector fails to pass through the origin 0 position of the X-Y coordinates due to temperature drift, the X-Y coordinates are moved through the microcomputer of the inspection apparatus 13 so as to enable the complex impedance vector to pass through the origin 0.

Figure 7:
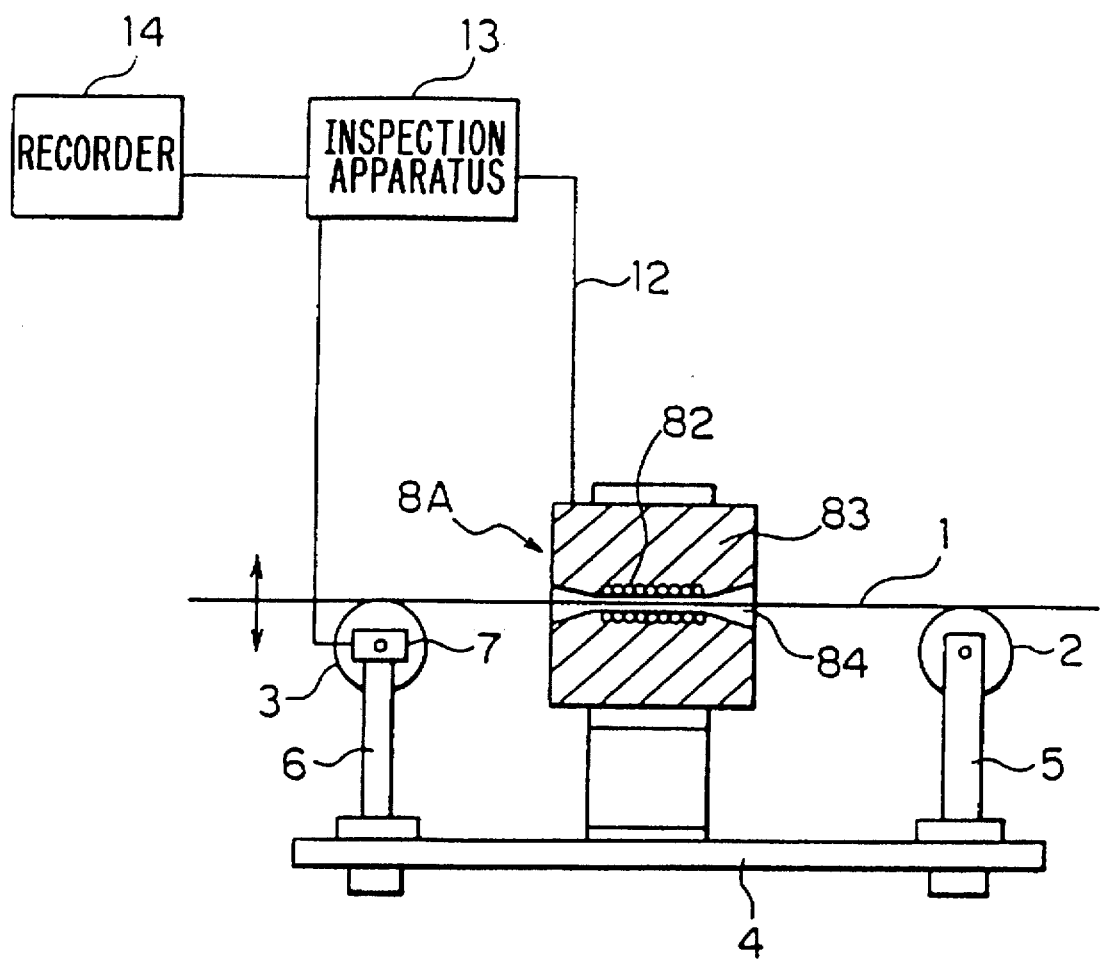
FIG. 7 is a constitutional view of a hermetic coating electrical resistance measurement system as a second embodiment of the electroconductive film inspection method of the present invention and an electroconductive film inspection system using the same.

FIG. 7 is a constitutional view of a hermetic coating electrical resistance measurement system as a second embodiment of the electroconductive film inspection method and electroconductive film inspection system of the present invention. This embodiment is one wherein the hermetically coated optical fiber 1 is made to pass through a hollow core type eddy current generation and inspection sensor 8A.

The constituent elements of the hermetic coating electrical resistance measurement system of FIG. 7 corresponding to the constituent elements of the hermetic coating electrical resistance measurement system of FIG. 2 are given the same reference numerals. The hollow core type eddy current generation and inspection sensor 8A has the outer periphery of the coil 82 molded integrally with a plastic 83 and is provided with a through hole 84 inside. The hollow core type eddy current generation and inspection sensor 8A is arranged horizontally and has a hermetically coated optical fiber 1 passed through its through hole 84.

In the second embodiment too, it is possible to measure the electrical resistance of the hermetic coating 1c in the hermetically coated optical fiber 1 in the same way as in the first embodiment.

Figure 8:
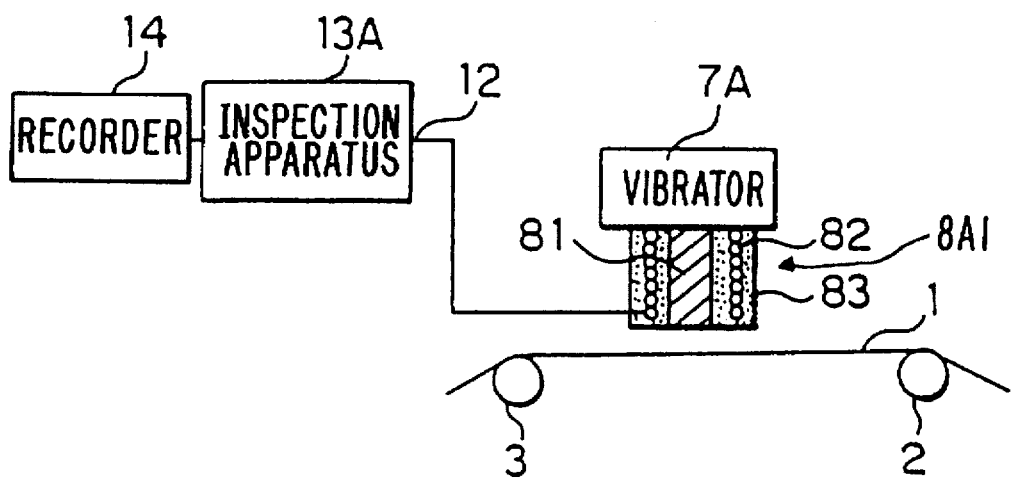
FIG. 8 is a constitutional view of a hermetic coating electrical resistance measurement system as a third embodiment of the electroconductive film inspection method of the present invention and an electroconductive film inspection system working the same.

FIG. 8 is a constitutional view of a hermetic coating electrical resistance measurement system as a third embodiment of the electroconductive film inspection method and electroconductive film inspection system of the present invention. The embodiment is one in which the eddy current generation and inspection sensor 8 is made to vibrate with respect to the hermetically coated optical fiber 1. This eddy current generation and inspection sensor 8A1 is constituted in the same way as the eddy current generation and inspection sensor 8 shown in FIG. 3.

The constituent elements of the hermetic coating electrical resistance measurement system of FIG. 8 corresponding to the constituent elements of the hermetic coating electrical resistance measurement system of FIG. 2 are given the same reference numerals. The eddy current generation and inspection sensor 8A1 is mounted to a vibrator 7A, which vibrator 7A is vibrated by the inspection apparatus 13A. As a result, reverse to the hermetic coating electrical resistance measurement system shown in FIG. 2, the eddy current generation and inspection sensor 8A1 vibrates up and down with respect to the hermetically coated optical fiber 1. The relationship of approach and distancing of the hermetically coated optical fiber 1 and the eddy current generation and inspection sensor 8A1, however, is the same as the case in the hermetic coating electrical resistance measurement system of FIG. 2. Therefore, even in the third embodiment, it is possible to calculate the electrical resistance of the hermetic coating 1c from the phase angle θ of the complex impedance in the same way as above in the inspection apparatus 13A.

The constituent conditions for the coil 82 in the eddy current generation and inspection sensor 8A1 in the third embodiment are shown in Table 3.

TABLE 3

| Inside diameter of coil 82 | 1.6 mm |
| Linear diameter of coil 82 | 0.05 mm |
| Number of turns of coil 82 | 180 |
| Length of coil 82 | 10 mm |

The frequency $f_1$ of the high frequency current for the generation of the eddy current applied to the coil 82 and the vibration frequency of the vibrator 7A are shown in Table 4.

TABLE 4

| Frequency f1 of high frequency current for generation of eddy current | 2 MHz |
| Vibration frequency of vibrator 7A | 60 to 100 Hz |

Figure 9:
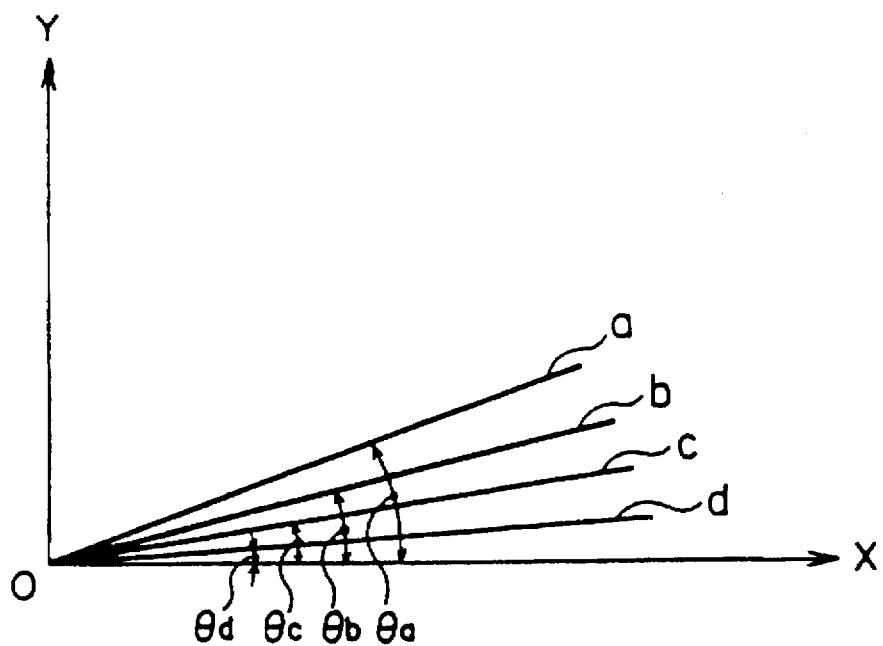
FIG. 9 is a characteristic graph showing the phase characteristic of the complex impedance measured in the electroconductive film inspection system of FIG. 8.

The results of measurement of the phase angles $θ_a$ to $θ_d$ shown in FIG. 9, measured as a result of experiments using hermetically coated optical fibers 1 coated with an amorphous carbon hermetic coating 1c as the samples a, b, c, and d and using the resistances per cm shown in the following Table 5 are shown in the following Table 5.

TABLE 5

| Sample | Resistance (kilohms/cm) | Phase angle |
|---|---|---|
| a | 4.6 | θa = 21 degrees |
| b | 7.0 | θb = 19 degrees |
| c | 9.3 | θc = 13 degrees |
| d | 18.5 | θd = 6 degrees |

Note that the thickness of the hermetic coating 1c of the sample a with a small resistance is large while the thickness of the hermetic coating 1c of the sample d with the large resistance is small. The inspection apparatus 13A calculates the electrical resistance of the hermetic coating 1c from the above-mentioned measured phase angles θ.

In the above embodiment, the explanation was made of an example of measurement of the electrical resistance of the hermetic coating 1c in the state with the hermetically coated optical fiber 1 running with respect to the eddy current generation and inspection sensor 8, but the eddy current generation and inspection sensor 8 may also be moved with respect to the hermetically coated optical fiber 1. Further, the same measurement as above may be performed with the eddy current generation and inspection sensor 8 and the hermetically coated optical fiber 1 in the stationary state.

Further, the electroconductive film inspection method and electroconductive film inspection system of the present invention are not limited to linear bodies such as hermetically coated optical fibers, but may be applied to plate shaped bodies as well and may also be applied to the inspection of other electroconductive films whose resistance can be measured using an eddy current, for example, a magnetic film.

Figure 10:
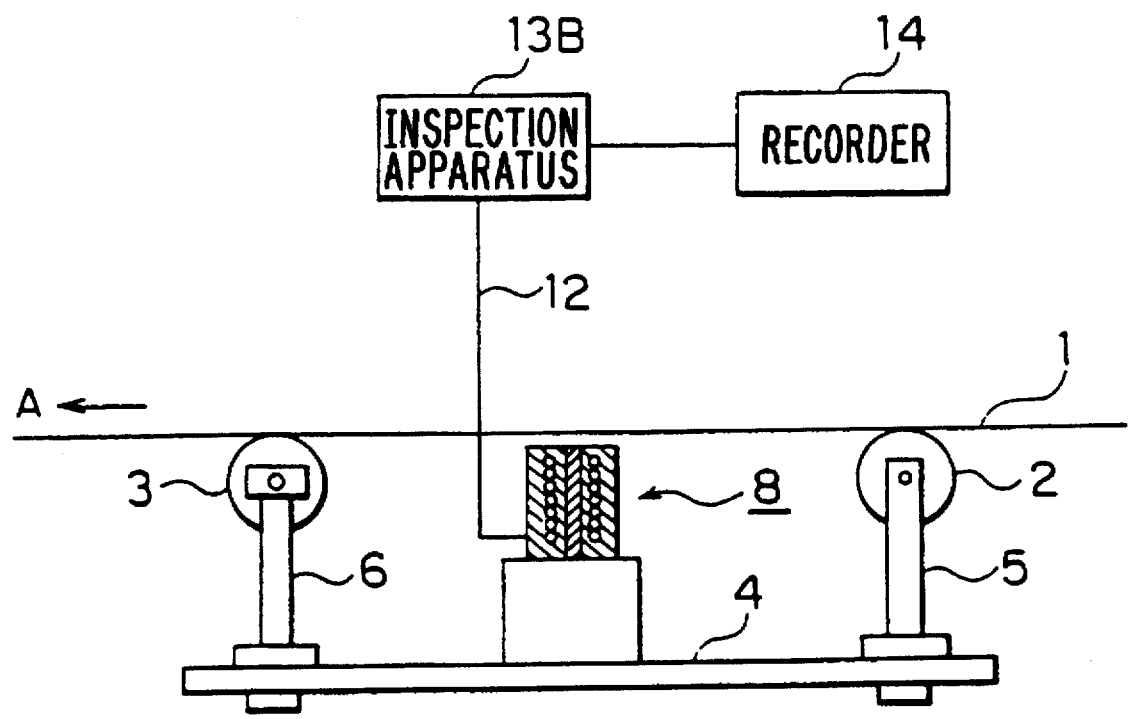
FIG. 10 is a constitutional view of a hermetic coating electrical resistance measurement system as a fourth embodiment of the electroconductive film inspection method of the present invention and an electroconductive film inspection system using the same.

FIG. 10 is a constituent view of a hermetic coating electrical resistance measurement system as a fourth embodiment of the electroconductive film inspection system using the electroconductive film inspection method of the present invention. Constituent elements in FIG. 10 the same as the constituent elements in FIG. 2 are given the same reference numerals.

The hermetic coating electrical resistance measurement system of FIG. 10 is not provided with the vibrator 7 shown in FIG. 2. The constitution and the functions of the inspection apparatus 13B differ from those of the inspection apparatus 13 of FIG. 2.

Figure 11:
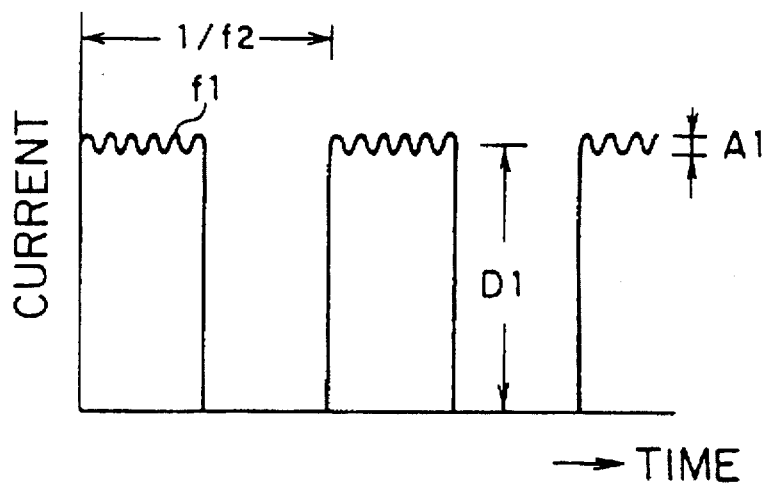
FIG. 11 is a waveform diagram of a current applied to an eddy current generation and detection coil in the hermetic coating electrical resistance inspection system shown in FIG. 10.

The hermetic coating electrical resistance measurement system does not change the distance between the above-mentioned hermetically coated optical fiber 1 and the eddy current generation and inspection sensor 8 by physical vibration, but changes the eddy current generated at the hermetic coating electrically by applying the high frequency current turning on and off as shown in FIG. 11 to the eddy current generation and inspection coil 8.

The inspection apparatus 13B has a power source which supplies to the inspection coil 82 of the eddy current generation and inspection sensor 8 an AC current of a high frequency $f_1$ sufficient for generating an eddy current in the hermetic coating 1c in the optical fiber 1. Alternatively, the inspection apparatus 13B has an addition circuit which is connected to a high frequency current generating power source and further adds to (superposes on) the high frequency current from the high frequency current generating power source an AC current having a low frequency, preferably, as mentioned later, a low frequency $f_2$ of less than 1/100th of the high frequency $f_1$ and of an amplitude larger than the amplitude of the high frequency AC current.

In the hermetic coating electrical resistance measurement system of the present invention, the explanation will be made of the case of using the eddy current generation and inspection sensor 8 shown in FIG. 3 for measurement of the electrical resistance of the hermetic coating 1c of the hermetically coated optical fiber 1 shown in FIG. 4. The conditions of the coil 82 of the eddy current generation and inspection sensor 8 are shown in Table 6 and the current conditions applied to the coil 82 and running speed of the hermetically coated optical fiber 1 are shown in Table 7.

TABLE 6

| Inside diameter of coil 82 | 1.6 mm |
| Linear diameter of coil 82 | 0.05 mm |
| Number of turns of coil 82 | 150 |
| Length of coil 82 | 10 mm |

TABLE 7

| | |
|---|---|
| Frequency $f_1$ of detection use high frequency current flowing to coil 82 | 2 MHz |
| Frequency $f_2$ turning on and off for changing average intensity of detection use current | 200 Hz |
| Running speed of optical fiber (linear speed) | 600 m/min |

In this embodiment, the average intensity of the detection use current, as shown in FIG. 11, is a frequency $f_2$=200 Hz sufficiently lower than the high frequency current frequency $f_1$=2 MHz and turned intermittently on and off. The frequency of the current of the on timing is a high frequency $f_1$, but the amplitude A1 is sufficiently smaller than the amplitude D1 when turned on and off.

This turning on and off is for detecting the eddy current at the on time and the eddy current at the off time and enabling accurate measurement of the phase angle of the complex impedance vector defined by these two points.

The amplitude A1 of the high frequency current in FIG. 11 may be an amplitude sufficient for generating an eddy current at the hermetic coating 1c, but in this embodiment the amplitude A1 is an effective value of 5 mA. Further, the amplitude D of the bias current for the discontinuation time need only be larger than the amplitude A1 of the high frequency current, but in this example is D1=500 mA.

Figure 12:
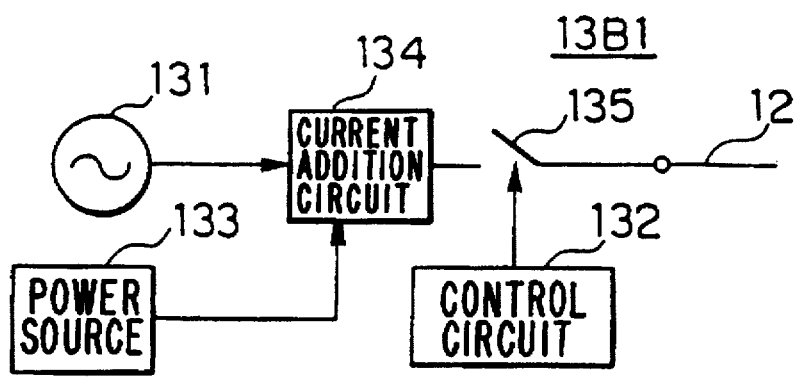
FIG. 12 is a constitutional view of the power supply circuit for generating the current shown in FIG. 11.

To satisfy the above-mentioned conditions, the inspection apparatus 13B has the power source circuit 13B1 shown in FIG. 12. The power source circuit 13B1 has a high frequency power source which is an AC power source 131 for generating a high frequency current of a high frequency $f_1$=2 MHz. The power source circuit further has an average magnetization-intensity changing means for applying the high frequency current from the AC power source to the eddy current generation and inspection sensor 8 while changing the average magnetization-intensity by a frequency sufficiently lower than the frequency of the high frequency current. The average magnetization-intensity means comprises a DC bias power source 133 for generating a DC bias current D1, a current addition circuit 134 for adding the high frequency current and DC bias current and switching means including a control circuit 132 for intermittently discontinuing the current from the current addition circuit 134 at a low frequency $f_2$=200 Hz and a switching circuit 135. If the control circuit 132 deenergizes the switching circuit 135 at the off timing, current is not applied to the coil 82 and an eddy current is not generated at the hermetic coating 1c.

Figure 1:
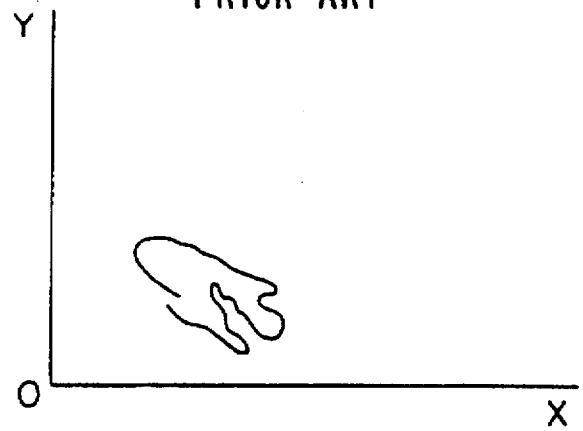
FIG. 1 is a view showing the locus of complex impedance obtained by a conventional eddy current inspection method.
Figure 13:
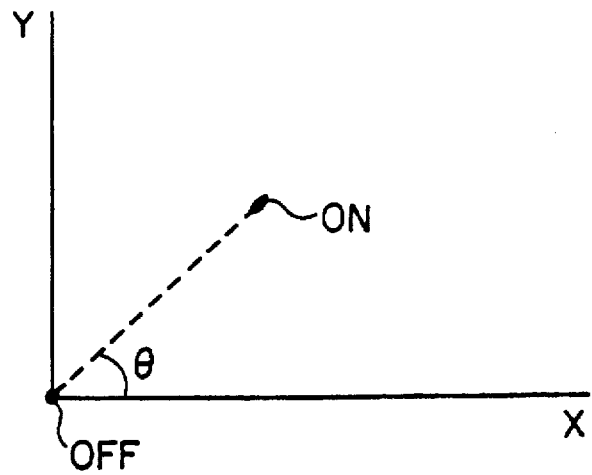
FIG. 13 is a characteristic graph showing the amplitude characteristic of the complex impedance measured by the electroconductive film inspection apparatus of FIG. 10 in the case of generating an eddy current at the hermetic coating using the current shown in FIG. 11.

If a high frequency current is applied to the coil 82 of the eddy current generation and inspection sensor 8, an eddy current is generated at the hermetic coating 1c and the coil 82 detects this. If the measurement values detected by the coil 82 are plotted by a recorder 14, as shown in FIG. 13, they are output as the complex impedance vector between two points ON and OFF with the phase angle θ including information of the electrical resistance of the hermetic coating 1c. The complex plane of FIG. 13, like the complex impedance plane of FIG. 1, shows the value of the real number portion of the complex impedance by the X axis and the value of the imaginary number portion of the complex impedance by the Y axis.

The output point ON at the on timing when the high frequency current is applied to the detection coil 82 of the eddy current generation and inspection sensor 8 is not a single exact point but extends in the direction of the phase angle θ due to the vibration accompanying the movement of the running hermetically coated optical fiber 1.

When the current applied to the eddy current generation and inspection sensor 8 goes off, the output becomes zero, so the origin of the X-Y coordinates is returned to, so zero point correction is performed each time at that time. Therefore, in this embodiment, the zero point of the output can be freed of the effects caused by temperature drifting.

Figure 14:
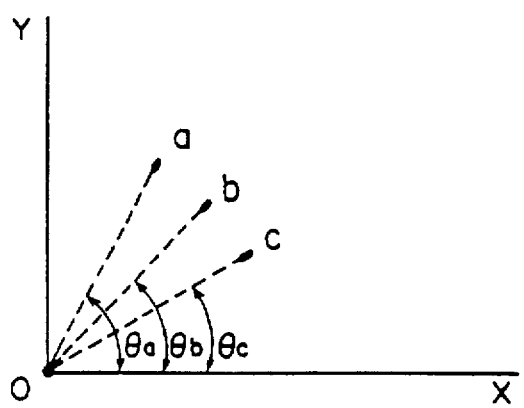
FIG. 14 is a characteristic graph showing the phase characteristic of the complex impedance measured by the electroconductive film inspection apparatus of FIG. 10 in the case of generating an eddy current at the hermetic coating using the current shown in FIG. 11.

FIG. 14 is a graph of the results of actual measurement of the phase angles $θ_c$ to $θ_c$ with respect to the samples a, b, and c for three types of hermetic coatings 1c with different resistances under the above inspection conditions. These phase angles $θ_c$ to $θ_c$ are the same as those shown in Table 5. The hermetic coatings of the samples a, b, and c were subjected to destructive tests after on-line measurement, whereupon they were found to have the same resistances as shown in Table 5.

The above results show that along with an increase in the electrical resistance of the hermetic coatings 1c (sample), the phase angle θ becomes smaller and that the phase angle θ is dependent on the electrical resistance of the samples.

Therefore, by mounting a microcomputer or other computing means in the control circuit 132 of the inspection apparatus 13B or by connecting a microcomputer or other computing means to the control circuit 132 for computation, it is possible to calculate the electrical resistance of the hermetic coating 1c reversely from the measured phase angle θ and further, using the above computing means, it is possible to automatically evaluate the state of formation of the hermetic coating 1c from the measured electrical resistance.

An explanation will now be made of another embodiment which uses the electroconductive film inspection system shown in FIG. 10 for measurement by current conditions different from the above-mentioned embodiment.

Figure 15:
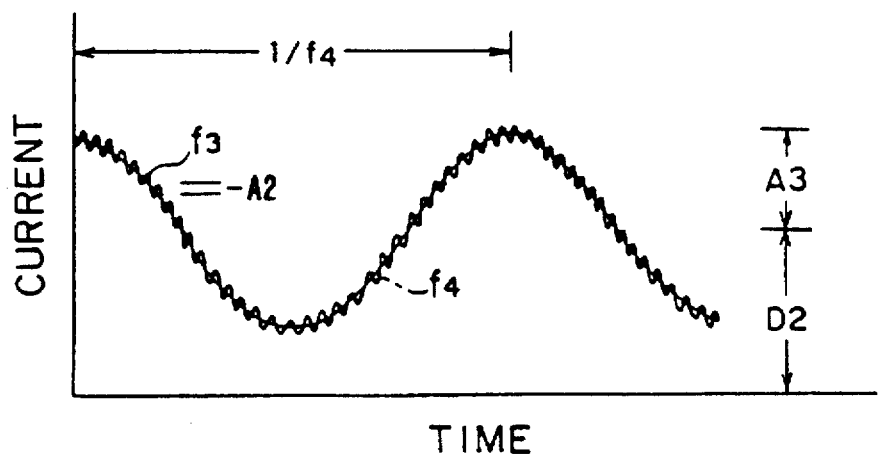
FIG. 15 is a waveform diagram of a current of another mode applied to an eddy current generation and detection coil in the electroconductive film inspection apparatus shown in FIG. 10.

In this embodiment, as shown in FIG. 15, use is made of a high frequency $f_3$ of 3 MHz for the detection use current flowing to the detection coil 82 of the eddy current generation and inspection sensor 8 and the average intensity of the detection use current is changed at a low frequency $f_4$=50 Hz. In the above embodiment, the high frequency current is turned on and off, but in this embodiment the amplitude is changed sinusoidally. In this example, the amplitude A2 of the high frequency current is an effective value of 3 mA, the amplitude A3 of the low frequency current is an effective value of 10 mA, and the DC bias current D2 is 20 mA.

Figure 16:
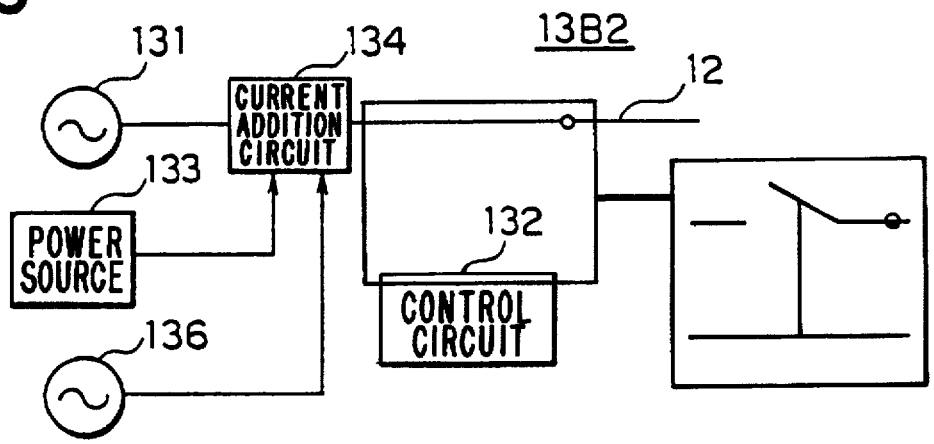
FIG. 16 is a constitutional view of the power supply circuit for generating the current shown in FIG. 15.

In this case, the inspection apparatus 13B has the power source 13B2 shown in FIG. 16. This power source circuit 13B2 has an AC power source (a high frequency power source) 131 of a high frequency $f_3$=3 MHz, a DC bias power source 133, an AC power source (a low frequency power source) 136 of a low frequency $f_4$=50 Hz, and, for example, a commercial frequency power source and further has an addition circuit 134 which adds the 3 MHz current and DC bias current D2 to the AC current of the low frequency=50 Hz. The added AC current is applied to the detection coil 82 of the eddy current generation and inspection sensor 8. In the inspection apparatus 13B too, the above-mentioned microcomputer-based computing means is built in or such a computing means is provided outside.

Figure 17:
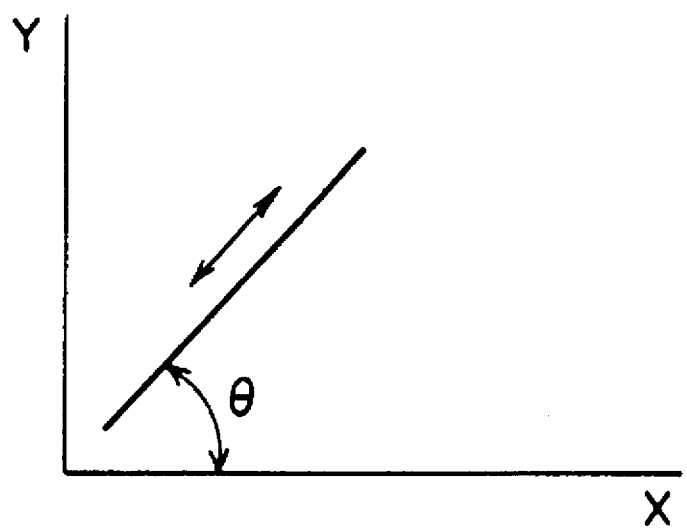
FIG. 17 is a characteristic graph showing the amplitude characteristic of the complex impedance measured by the electroconductive film inspection apparatus of FIG. 10 in the case of generation of an eddy current at the hermetic coating using the current shown in FIG. 15.

In this case too, as shown in FIG. 17, if the results of the detection are plotted using the recorder 14 on the complex impedance plane, it is possible to detect two eddy currents at the two points of the maximum amplitude and minimum amplitude of the current applied to the coil 82, but the output changes with a certain phase angle θ in accordance with the resistance of the hermetic coating 1c.

By adjusting the DC bias of the DC bias current 133, when the output point approaches the origin (zero point), it is possible to correct the line of change of the signal to pass through the zero point. Further, even without correction, if only the direction of the complex impedance vector, that is, the phase angle θ, is measured, stable measurement becomes possible without regard to drift of the zero point.

The results of measurement of the phase angle θ for the electrical resistances of the hermetic coatings 1c are the same as in the above embodiment are as follows:

TABLE 8

| Phase angle $\theta_a$ of sample a | 26 degrees |
|---|---|
| Phase angle $\theta_b$ of sample b | 21 degrees |
| Phase angle $\theta_c$ of sample c | 16 degrees |

These results also show that the phase angle θ decreases along with an increase in the electrical resistances of the samples and that there is a certain correlative relationship between the electrical resistance and the phase angle θ of the hermetic coating 1c.

Figure 18:
FIG. 18 is a characteristic graph showing changes in the electrical resistance of the hermetic coating under the same formation conditions as at the step of formation of the hermetic coating.

FIG. 18 shows the results of continuous measurement of the electrical resistance of the hermetic coating 1c in the process for forming the hermetic coating 1c of the hermetically coated optical fiber 1 having the sectional structure shown in FIG. 3. The horizontal axis of FIG. 18 shows the elapse of time, while the vertical axis shows the magnitude of the phase angle θ. In this example, the concentration of the material gas is successively lowered, so the thickness of the hermetic coating 1c becomes smaller and the electrical resistance of the hermetic coating 1c becomes higher and as a result the phase angle θ becomes successively smaller. If this method is used, it becomes possible to continuously measure the phase angle θ and, when the phase angle θ falls out of a predetermined range, to control the material gas feed conditions, reaction temperature, and other conditions of formation of the hermetic coating so as to form a uniform hermetic coating. This will be explained later.

Further, when investigating the case where the frequency $f_1$ of the detection use high frequency current was 3 MHz and the average intensity of the same was changed by a low frequency $f_2$ of 100 kHz, that is, about 1/30th of the above detection use current frequency of 3 MHz, the measurement precision conspicuously deteriorated. Therefore, from the above test results, it is desirable that the average intensity, resulting from the high frequency current flowing to the coil 82, be changed by a low frequency of no more than 1/100th of the high frequency $f_1$. The changes in the average intensity result from the intermittent turning on and off as shown in FIG. 11.

The above embodiment was explained with respect to an example of inspection of the state of formation by measurement of the electrical resistance of the hermetic coating 1c continuously and on-line without removing the protective plastic coating formed on the outer surface of the hermetic coating of a running hermetically coated optical fiber 1 and without contact with the hermetic coating 1c of the optical fiber during production, but the present invention can also be effectively applied to an optical fiber or other linear body when not running, i.e., in a stationary state.

Further, the electroconductive film inspection method of the present invention and electroconductive film inspection system using the same are not limited to inspected objects which are linear bodies like optical fibers, but can also be used for the case of on-line, continuous inspection of the state of formation of magnetic films.

Note that the present invention is suitable for measurement of the electrical resistance of a thin film conductor, but is not limited to a thin film and can be widely used for electroconductive films using eddy currents.

As explained above, according to the electroconductive film inspection method and apparatus of the present invention, it is possible to measure the electrical resistance of an inspected object, that is, an electroconductive film, without regard to whether it is stationary or moving, in a nondestructive state, without contact, continuously, automatically, and stably at a high precision.

The electrical resistance shows the state of formation of the electroconductive film. It is possible to evaluate on-line automatically the state of formation from the electrical resistance.

Therefore, by using the electroconductive film inspection method of the present invention and the system thereof, it is possible to not only inspect the hermetically coated optical fiber cable after production but also to continuously test and evaluate, on-line, the state of formation of a hermetic coating 1c at the step of formation of the hermetic coating.

Figure 19:
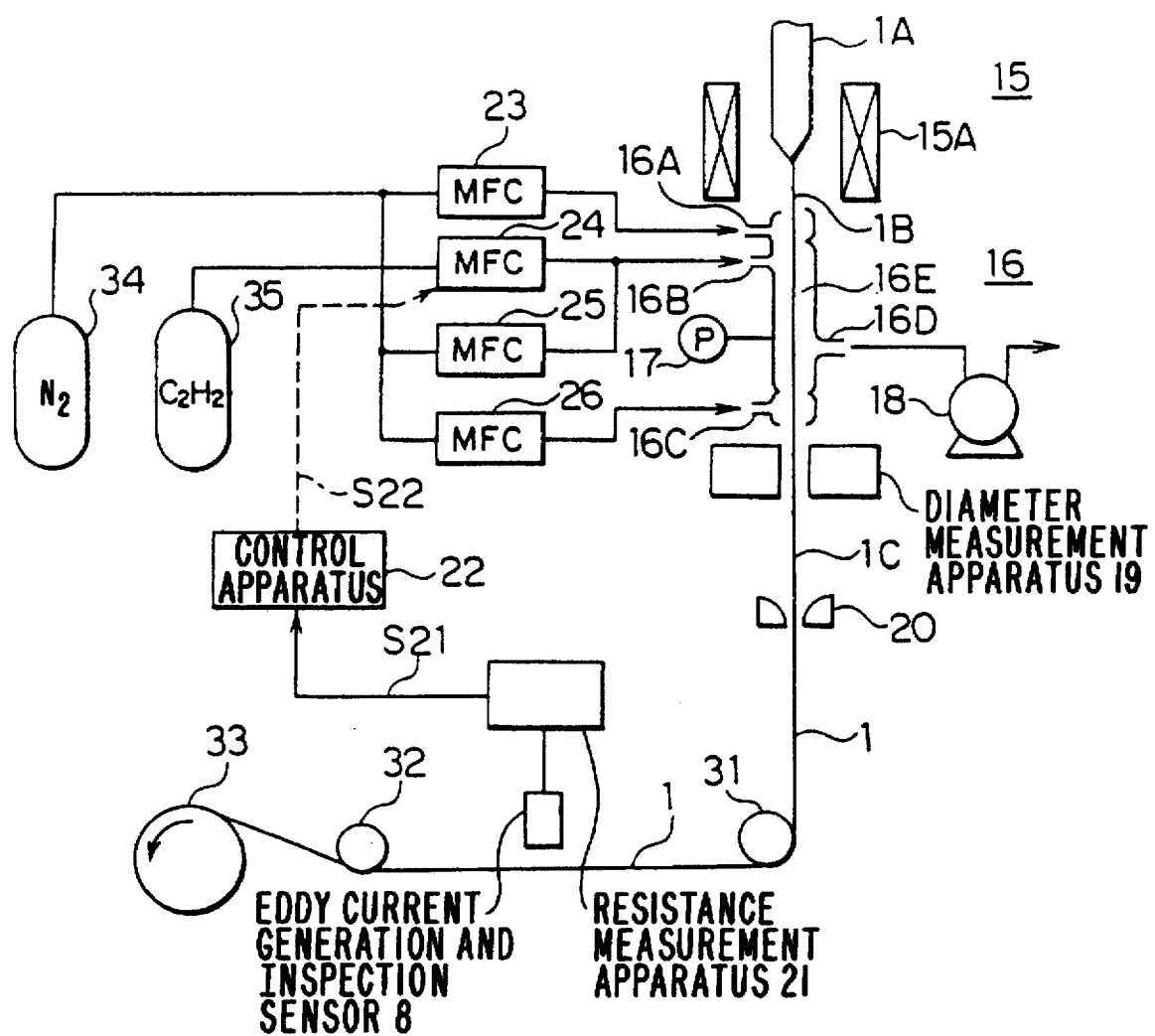
FIG. 19 is a constitutional view of an optical fiber production system as a first embodiment of the electroconductive film production process using the electroconductive film inspection method of the present invention and the electroconductive film production system using the same.

FIG. 19 is a constituent view of an optical fiber production system as a first embodiment of an electroconductive film production process and production system using the above-mentioned electroconductive film production process of the present invention.

The optical fiber production system is for forming an optical fiber line 1B comprised of a core 1a and a cladding 1b by drawing (spinning) an optical fiber preform 1A and has a drawing furnace 15 with a heater 15A disposed therein, a reaction tube (reaction furnace) 16, a laser fiber outer diameter measurement apparatus 19, a plastic coating die, a capstan roller 31, a dancer roller 32, and a takeup drum 33. The optical fiber production system further has a gas tank 34 filled with an inert gas used as a sealing gas or dilution gas, in this embodiment, nitrogen ($N_2$) gas, a gas tank 35 filled with a hermetic coating forming material gas, in this embodiment, acetylene ($C_2H_2$) gas, and mass flow controllers (MFC) 23 to 26 for controlling the flow of the same. The optical fiber production system further has an eddy current generation and inspection sensor 8, an electrical resistance measurement apparatus 21 for supplying high frequency current to the coil 82 of the eddy current generation and inspection sensor 8 and measuring the electrical resistance of the hermetic coating 1c, and a process control apparatus 22. The electrical resistance measurement apparatus 21 corresponds to the above-mentioned inspection apparatuses 13, 13B, etc.

The reaction tube 16 has an upper sealing gas inlet 16A for filling the sealing gas, i.e., $N_2$ gas, into the upper sealing zone from the nitrogen gas tank 34 and a lower sealing gas inlet 16C for filling $N_2$ gas into the lower sealing zone. The mass control of the sealing gas is performed by the MFC's 23 and 26. At the bottom of the upper sealing gas inlet 16A is provided the material gas inlet 16B. $C_2H_2$ is introduced as the material gas and $N_2$ gas as the dilution gas by these MFC 24 and MFC 25 to the reaction tube 16E. Used gas is discharged by an exhaust pump 18 from the discharge port 16D.

The inside space 16E between the upper sealing gas inlet 16A and the lower sealing gas inlet 16C is the reaction portion 16E for forming the hermetic coating 1c. A pressure sensor 17 is provided for measuring the pressure of the reaction portion 16E.

The preform 1A is drawn into a line by the drawing furnace 15 to form an optical fiber line 1B having a cross-section as shown in FIG. 4 and, for example, a core 1a of a diameter of 10 microns and a cladding 1b of an outer diameter of 125 microns formed at the outside of the core 1a.

The optical fiber line 1B is introduced into the reaction tube 16 and the heat of the optical fiber line 1B itself just after being led out of the drawing furnace 15 or that heat and the heat from a heater (not shown) disposed outside of the reaction tube 16 are used for a heating reaction of the acetylene gas ($C_2H_2$) gas introduced into the reaction tube 16B so that carbon is precipitated on the surface of the cladding 1b and an amorphous carbon hermetic coating 1c of a thickness of 500 to 1000 Å is formed. The result is drawn out of the reaction tube 16 as the naked optical fiber line 1C. The MFC's 24 and 25 perform suitable mass (flow rate) control of the $C_2H_2$ gas and $N_2$ gas so that the hermetic coating 1c is formed.

The naked optical fiber line 1C is measured as to its outer diameter when passing through the laser outer diameter measurement apparatus 19.

The optical fiber 1c passing through the laser outer diameter measurement apparatus 19 has deposited on it, at the plastic coating die 20, a plastic coating as a protective coating 1d to form the hermetically coated optical fiber 1. The hermetically coated optical fiber 1 is conveyed via the capstan roller 31 and dancer roller 32 and taken up on a takeup drum 33.

In the embodiment, the capstan roller 31 and dancer roller 32 have arranged between them and close to the moving hermetically coated optical fiber 1 the eddy current generation and inspection sensor 8 which measures on-line the electrical resistance of the hermetic coating 1c in a noncontact state from the outside of the plastic coating 1d.

The sectional structure of the eddy current generation and inspection sensor 8 is the same as the structure shown in FIG. 3.

The electrical resistance measurement apparatus 21 has the same type of power source circuit as the power source circuit 13B1 shown in FIG. 12. The current of the waveform shown in FIG. 11 from the power source circuit is applied to the coil 82 of the eddy current generation and inspection sensor 8.

In this embodiment too, the average intensity of the eddy current detection current, as shown in FIG. 11, has the frequency $f_2$=200 Hz, sufficiently smaller than the high frequency $f_1$=2 MHz and the high frequency detection current is turned on and off intermittently. The frequency of the current at the on timing is the high frequency $f_1$=2 MHz, but the amplitude is sufficiently smaller than the amplitude at the turning on and off. As mentioned above, the turning on and off is for detecting the eddy current at the on time and the eddy current at the off time and enabling accurate measurement of the phase angle of the complex impedance vector defined by these two points.

The results of the measurement are the same as shown in Table 5 and Table 8.

Figure 20:
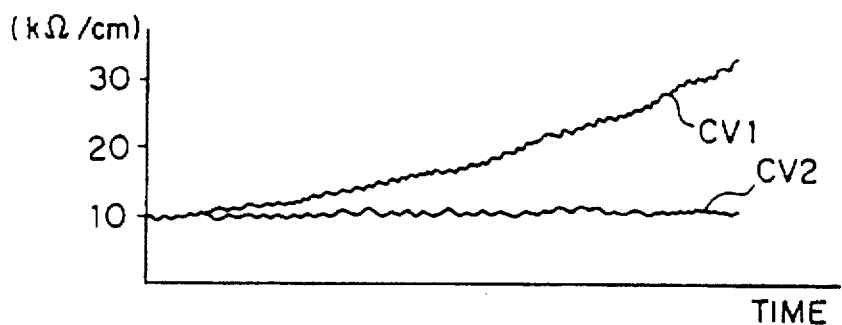
FIG. 20 is a characteristic graph showing changes over time of the electrical resistance of a hermetic coating produced in the optical fiber production system shown in FIG. 19.

FIG. 20 shows the changes in the electrical resistance of the hermetic coating 1. The curve CV1 shows the changes when the MFC 24 introduces $C_2H_2$ gas into the material gas feed inlet 16B under the same set conditions.

The production conditions of the optical fiber at this time are shown below:

TABLE 9

| | |
|---|---|
| Temperature of drawing furnace 15 | 2100° C. |
| Drawing speed | 600 m/min |
| Pressure inside reaction tube 16 | −30 mmAq |
| Sealing gas flow rate | 10 liters/min |
| Material gas flow rate | 1 liter/min |
| Dilution gas flow rate | 9 liters/min |

Normally, the electrical resistance of the hermetic coating 1c is around 10 kilohms/cm, but the curve CV1 shows that even when the MFC 24 is at the same setting, the electrical resistance of the hermetic coating 1c increases along with the passage of time, in other words, the thickness becomes smaller. As the reason for this, it is believed that along with the elapse of time, carbon adheres to the inside walls of the reaction tube 16E making the tube diameter smaller and increasing the flow rate of the gas, so the amount of carbon adhering to the outer surface of the cladding 1b becomes smaller.

To adjust on-line the state of formation of the above-mentioned hermetic coating 1c, in the present invention, the electrical resistance of the hermetic coating 1c calculated at the electrical resistance measurement apparatus 21 is output to control means in this instance the process control apparatus 22.

The process control apparatus 22 outputs control commands to the MFC 24 so that the electrical resistance becomes in a predetermined range, for example, 10 kilohms/cm. The MFC 24 reduces the flow rate of the $C_2H_2$ introduced from the acetylene gas tank 35 to the reaction portion 16E based on the control commands from the process control apparatus 22 so that an amorphous carbon coating 1c with a predetermined thickness is formed on the outer surface of the cladding 1b.

In this way, the flow rate of the $C_2H_2$ gas is controlled to maintain the electrical resistance of the hermetic coating 1c to about 10 kilohms/cm as shown by the curve CV2 of FIG. 20 and to make the thickness of the hermetic coating 1c, for example, 1000 Å.

In this way, by feeding back the measured electrical resistance of the hermetic coating 1c formed by introducing the $C_2H_2$ gas to the control conditions of the process for forming the hermetic coating 1c, it is possible to accurately form the thickness of a hermetic coating 1c formed continuously and it is possible to realize excellent quality control.

Figure 21:
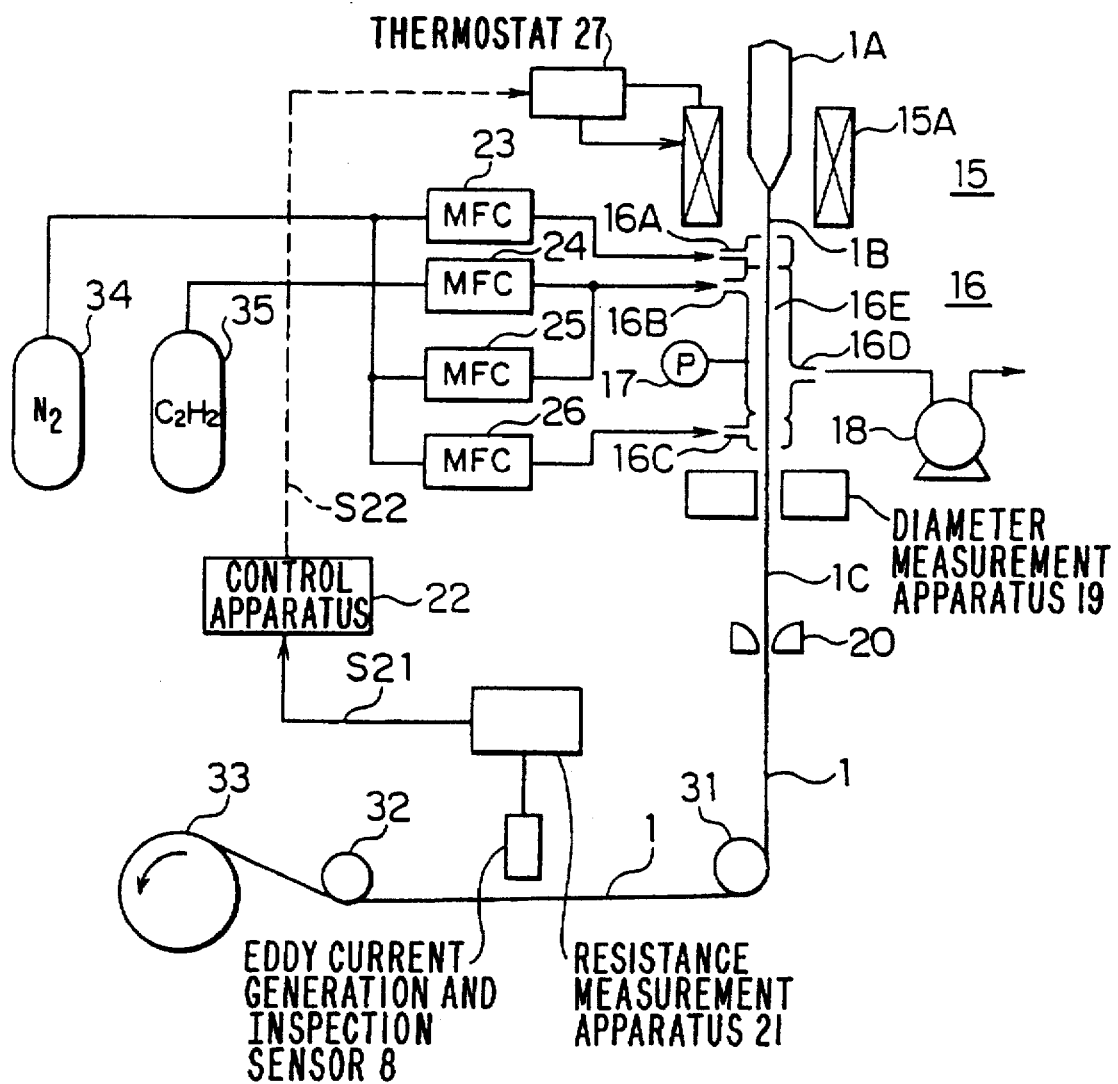
FIG. 21 is a constitutional view of an optical fiber production system as a second embodiment of the electroconductive film production process using the electroconductive film inspection method of the present invention and an electroconductive film production system using the same.

FIG. 21 shows an optical fiber production system as a second embodiment of an electroconductive film production system for working an electroconductive film production process using the electroconductive film production process of the present invention.

This embodiment, as clear from a comparison with the construction of the optical fiber production system shown in FIG. 19, is comprised so that the settings of a thermostat 27 controlling the heater 15A are changed based on the feedback signals S22 from the process control apparatus 22. That is, this embodiment does not control the carbon flow rate directly as in the first embodiment, but controls the drawing temperature at the drawing furnace 15.

Figures 22A, 22B, 22C:
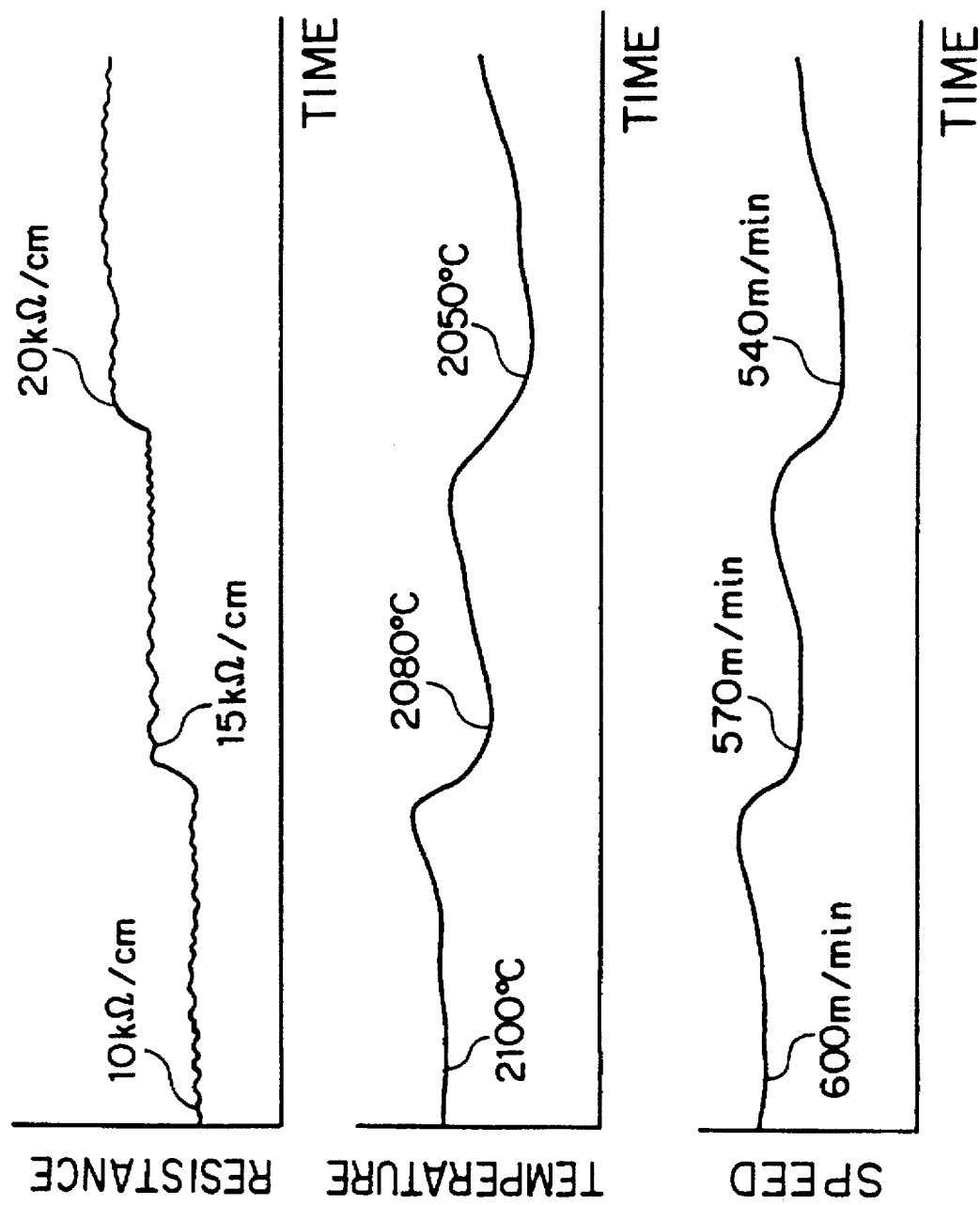
FIGS. 22(A) to 22(C) are characteristic graphs showing the conditions for forming a hermetic coating in the optical fiber production system of FIG. 21.

FIGS. 22(A) to 22(C) show the relationship between the electrical resistance and the drawing temperature. These figures show the drawing temperature and line speed at electrical resistances of 10, 15, and 20 kilohms. If the drawing temperature is reduced, the diameter of the optical fiber line 1B becomes smaller and the line speed becomes slower. By this, it is possible to effectively reduce the decomposition temperature of the material gas. Further, as mentioned with reference to the first embodiment, the electrical resistance rises due to the changes in the reaction tube 16E, so in the individual set conditions, the drawing temperature is gradually raised so that the electrical resistance of the hermetic coating 1c is constant.

In the working of this invention, it is possible to combine the above first embodiment and second embodiment.

Further, in FIG. 19 and FIG. 21, the eddy current generation and inspection sensor 8 may be placed between the plastic coating die 20 and capstan roller 31. Further, in the present invention, the eddy current generation and inspection sensor 8 and the hermetic coating 1c do not contact each other, so may be placed between a laser outer diameter measurement apparatus 19 and plastic coating die 20, making it possible to measure the electrical resistance of the hermetic coating 1c as well.

Further, the high frequency current applied to the eddy current generation and inspection sensor 8 may be that shown in the above-mentioned FIG. 11 and in addition the current shown in FIG. 15 may be applied.

The current waveform of FIG. 15, as mentioned above, is one formed by using 3 MHz as the frequency $f_1$ of the detection use current flowing to the eddy current generation and inspection sensor 8 and changing the average intensity of the detection use current by the low frequency $f_2$=50 Hz. In this embodiment too, the amplitude A2 of the high frequency current is an effective value of 3 mA, the amplitude A3 of the low frequency current is an effective value of 10 mA, and the DC bias current D2 is 20 mA.

An explanation will now be made of another embodiment for measuring the electrical resistance of the hermetic coating 1c without contact and on-line.

Figure 23:
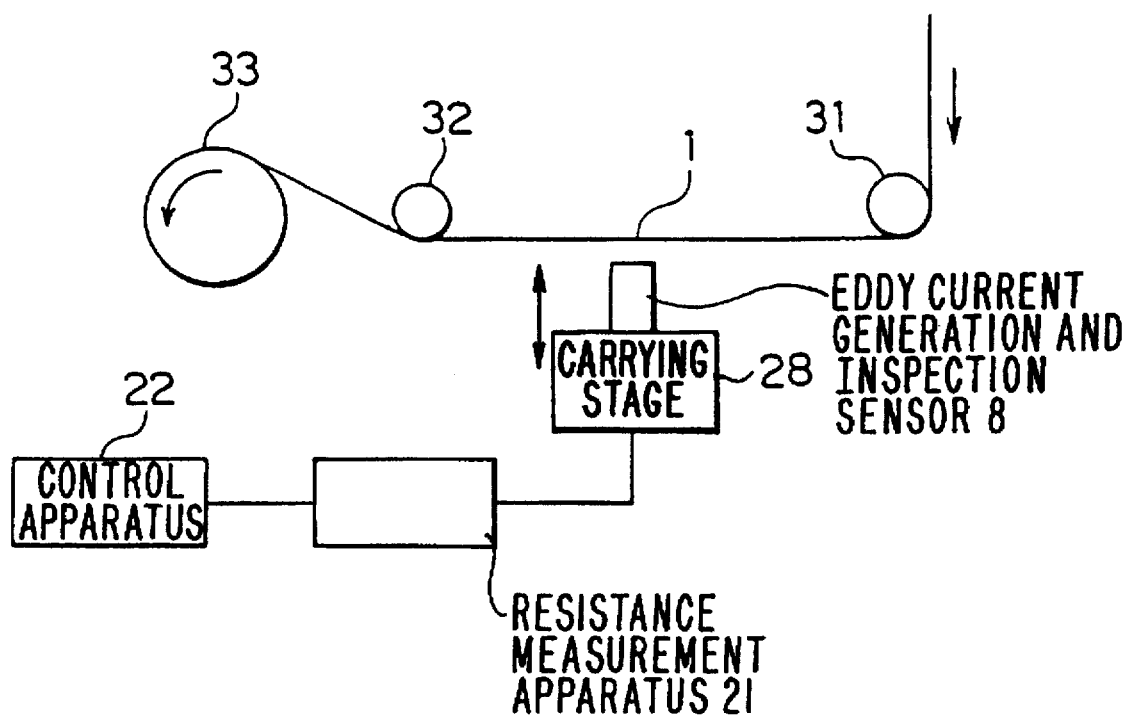
FIG. 23 is a partial constitutional view of an optical fiber production system as a third embodiment of the electroconductive film production system of the present invention.

FIG. 23 shows the partial constitution of the optical fiber production system shown in FIG. 19 and FIG. 21. In this embodiment, the electrical resistance measurement apparatus 21 causes vibration of a vibration stage 28 disposed between a capstan roller 31 and dancer roller 32 at a vibration frequency of a low vibration frequency=200 Hz or so, about 1/100th of the high frequency current generating an eddy current, so as to cause vibration of the eddy current generation and inspection sensor 8 carried on the carrying stage 28 near the moving hermetically coated optical fiber 1. This vibration substantially equivalently changes the average power by adding the above-mentioned high frequency current to the low frequency current. Therefore, it is possible by this method too to accurately measure without contact and on-line the electrical resistance of the hermetic coating 1c in the moving hermetically coated optical fiber 1.

Note that the eddy current generation and inspection sensor 8 may also be fixed in place and a moving hermetically coated optical fiber 1 made to vibrate with respect to the eddy current generation and inspection sensor 8.

The above embodiment illustrates the case of forming an amorphous carbon coating as the hermetic coating, but the process and apparatus of the present invention mentioned above may be applied to any electroconductive coating. Therefore, for example, it is possible to use the present invention for the production of cables etc. having electroconductive coatings such as aluminum.

As explained above, according to the electroconductive film production process and the electroconductive film production system of the present invention, it is possible to measure without contact and on-line the electrical resistance of an electroconductive film, such as the electroconductive hermetic coating in a moving hermetically coated optical fiber, and possible to feed back the results to the process for forming the electroconductive film, so it is possible to form an electroconductive film satisfying predetermined conditions without the influence of changes of the conditions for forming the electroconductive film and possible to prevent in advance the occurrence of defective products.

An explanation will be made of a method and system for inspection of the state of formation of an electroconductive film as still another embodiment of the present invention.

In the field of semiconductors, use is made of a high resistance semiconductor substrate (wafer) on which is grown by chemical vapor deposition or other processes an electroconductive layer doped with impurities and on which is formed electronic devices and optical devices. In the use of these, it is important how many devices of the same quality are formed from a single substrate. Therefore, it is required that the thickness and the electrical characteristics be uniform over the entire substrate. In actuality, however, there are variations in the thickness and electrical properties and the quality of the substrate as a whole is determined by them.

In the past, a large number of substrates of the same lot were used to simultaneously produce film covered substrates and then certain substrates were sampled out of them and destroyed for inspection and analysis of the thickness and electrical characteristics, with the results of the inspection and analysis used to estimate the quality of the substrates in the lot as a whole. Sometimes, however, there were substrates which did not reach the standards of quality and such inferior quality of substrates could not be detected. If a substrate was a transparent member like a display glass plate, optical measurement of the thickness is possible, but it was impossible to measure the electrical characteristics such as the electrical resistance.

This situation was the same for magnetic films.

In a method and system for inspection of the state of formation of an electroconductive film of the present invention, in the same way as with the evaluation of the thickness of the hermetic coating of an optical device mentioned above, an eddy current is generated in the above-mentioned semiconductor substrate film or magnetic film in a noncontact state and the eddy current is measured to measure the electrical resistance of the film. When measuring the electrical resistance of the film, the eddy current generation and inspection sensor is run in a inspected is run in a noncontact state in two-dimensions with respect to a fixed eddy current generation and inspection sensor for measurement over the entire film.

Figure 24:
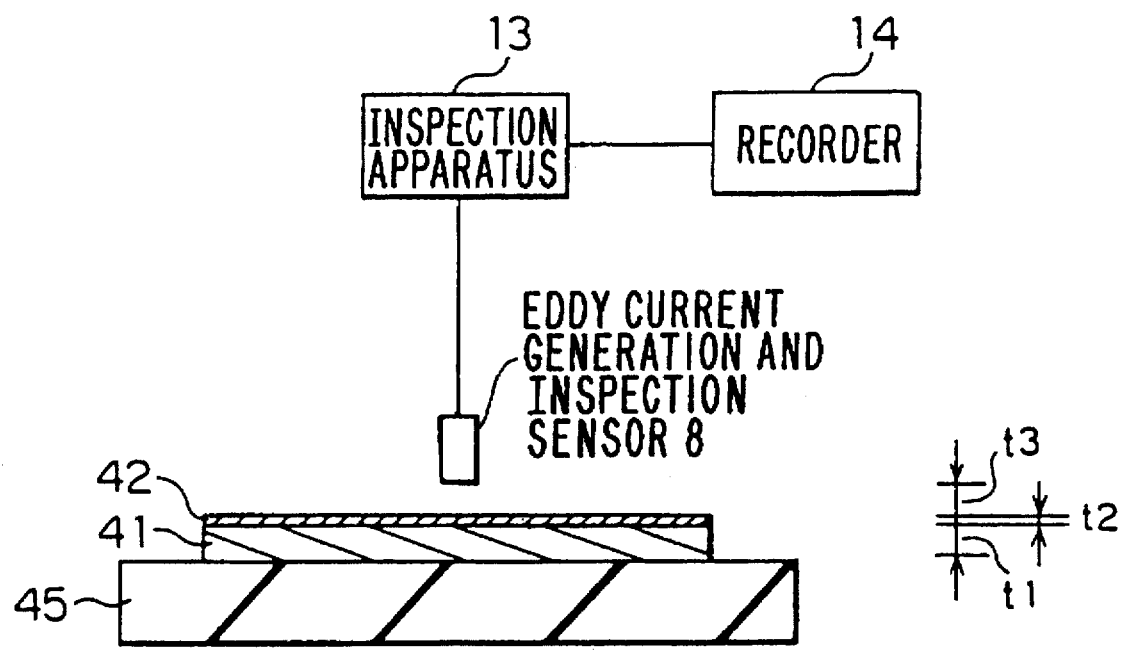
FIG. 24 is a constitutional view of an embodiment of the formation state inspection system of an electroconductive film of the present invention.

FIG. 24 shows a constitutional view of an embodiment of a system for inspection of the state of formation of an electroconductive film of the present invention. In the formation state inspection system of an electroconductive film, use is made of the above-mentioned inspection apparatus 13, recorder 14, and eddy current generation and inspection sensor 8 so as to measure the electrical resistance of the active layer 42 formed on the surface of a wafer 42 placed on a moving stage 45.

Figure 25:
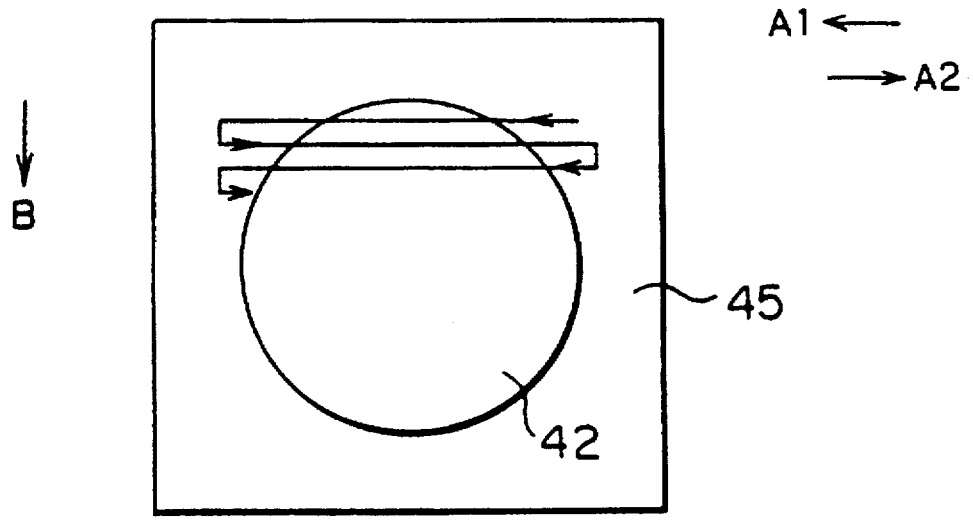
FIG. 25 is a view showing the locus formed by the eddy current generation and inspection sensor's scanning of the active layer formed on a wafer inspected in FIG. 24.

The moving stage 45, as shown in FIG. 25, is moved in the direction A1, is moved in the direction B a predetermined distance, and is moved in the direction A2 reverse to the direction A1. This movement operation is repeated so that the entire surface of the active layer 42 is swept. The movement distance in the direction B is made a distance sufficient for generation and detection of the eddy current. The movement of the moving stage 45 is controlled using a microcomputer in the inspection apparatus 13.

In this embodiment too, the phase angle θ of the complex impedance vector showing the thickness and electrical resistance at a position of the active layer 42 detected by the eddy current generation and inspection sensor 8 in the process of movement of the moving stage 45 becomes as shown in FIG. 13 and is recorded in the recorder 14.

In this embodiment, the distance t3 between the eddy current generation and inspection sensor 8 and active layer 42 is 500 microns, the thickness t2 of the active layer 42 is 0.5 micron, and the thickness t1 of the wafer 41 is 0.4 mm. Note that the amplitude between the two points changes depending on the distance t3 between the eddy current generation and inspection sensor 8 and the active layer 42.

Figure 26:
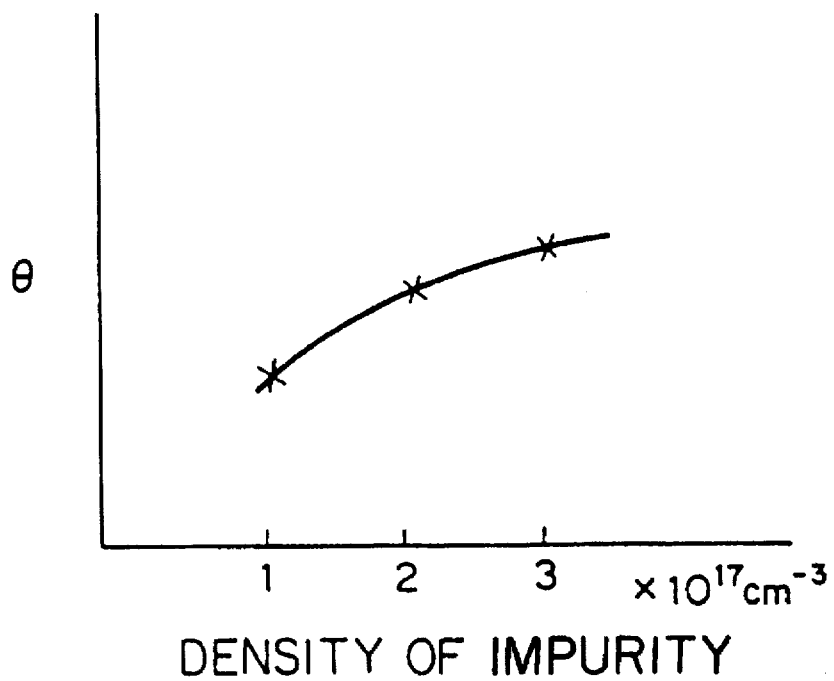
FIG. 26 to FIG. 28 are graphs of the active layer obtained by the formation state inspection system of the electroconductive film of FIG. 24.
Figure 27:
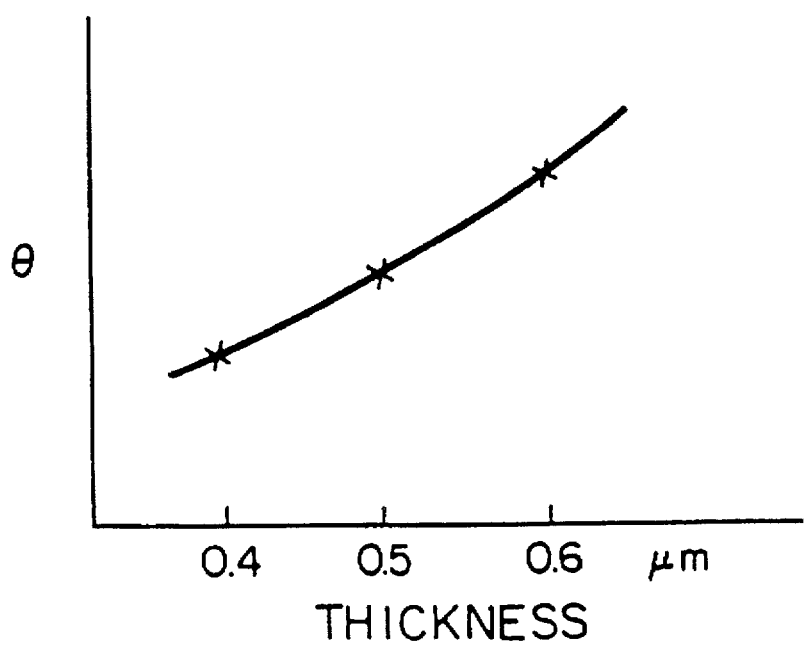

FIG. 26 and FIG. 27 show graphs based on the present embodiment.

FIG. 26 shows the changes (vertical axis) in the phase angle θ when growing on a GaAs substrate, used as the wafer 41, a nondoped GaAs, AlGaAs film as an active layer 42, then growing sulfur S-doped GaAs to 0.5 micron and changing the concentration of impurities (horizontal axis) to $1\times10^{17}$ cm$^{-3}$, $2\times10^{17}$ cm$^{-3}$, and $3\times10^{17}$ cm$^{-3}$. The higher the concentration of impurities, the smaller the relative resistance of the semiconductor, and as a result, the smaller the resistance and the larger the phase angle θ. FIG. 27 shows the changes (vertical axis) of the phase angle θ when fixing the concentration of impurities to $2\times10^{17}$ cm$^{-3}$ and changing the thickness t2 (horizontal axis) to 0.4 micron, 0.5 micron, and 0.6 micron. The larger the thickness t2, the smaller the resistance in the surface direction and the larger the value of the phase angle θ. The above results are calculated by the inspection apparatus 13. Therefore, in the inspection apparatus 13, it is possible to determine the thickness of the active layer 42 and the concentration of impurities.

Figure 28:
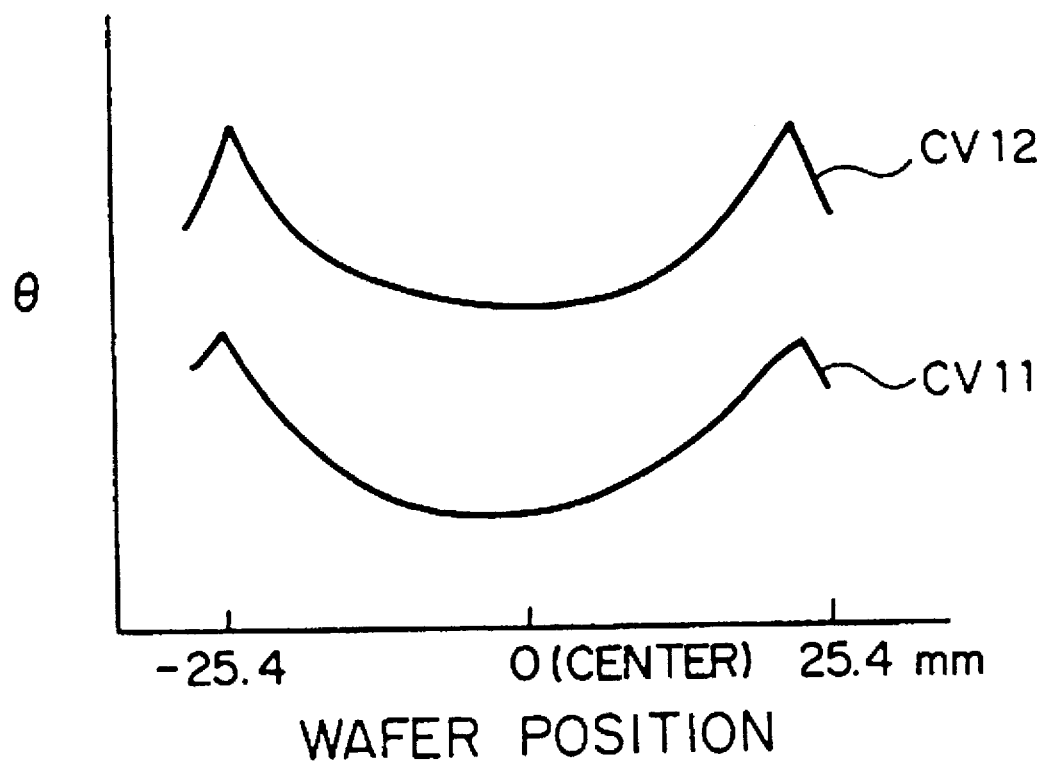

The wafer temperature has an effect on the concentration of the dopant and the distribution of thickness and in particular has a large effect on the concentration of the dopant. Therefore, even if the thickness distribution is constant, a spread appears in the concentration of the dopant. The graph of FIG. 28 shows this feature. In the figure, the horizontal axis shows the wafer position and the vertical axis the phase angle θ. The thickness t2 of the wafer is fixed at 0.5 micron. The curves CV11 and CV12 show the changes in the phase angle θ due to the change of the concentration of impurities n1 and n2. Further, the phase angle θ changes depending on the wafer position. By scanning the wafer as a whole by the sensor 8, it is possible to evaluate overall that wafer.

Note that in the above embodiment, instead of moving the moving stage 45, it is possible to move the eddy current generation and inspection sensor 8 as shown in FIG. 25 and scan the active layer 42 as a whole.

In the above embodiment, the explanation was made of an example of formation of an active layer 42 on the wafer 41, but similar results were obtained in the case of measurement of the resistance of an ITO film doped with $SnO_2$ and on a glass plate.

In the above embodiment, it was not attempted to change the distance t3 between the eddy current generation and inspection sensor 8 and the active layer 42. Further, no change was made in the average intensity of the high frequency current applied to the eddy current generation and inspection sensor 8 through the inspection apparatus 13.

When measuring at a high density with the distance of measurement on the plane of the active 42 being made smaller, the measurement time sometimes is a long time of from several minutes to several tens of minutes. In such long time measurement, the problem sometimes occurs in the high frequency electrical system of the inspection apparatus 13 of zero drift due to temperature changes etc. If the measurement values in this case are plotted, the result becomes as shown in FIG. 1. To eliminate the problem of drift, as mentioned above, the distance between the eddy current generation and inspection sensor 8 and the active layer 42 is changed at a period sufficiently lower than the high frequency of the high frequency current applied to the eddy current generation and/or the average intensity of the high frequency current applied to the eddy current generation and inspection sensor 8 is changed at a low frequency. Therefore, the inspection apparatus 13 is constructed as explained above.

We claim:

1. A production apparatus for producing an optical fiber cable including an optical fiber having a core and a cladding, and a coating, said production apparatus comprising:

a drawing furnace for drawing an optical fiber preform and forming said optical fiber having said core and said cladding;

a reaction furnace, which has introduced in it a hermetic coating forming material gas and said optical fiber drawn from said drawing furnace, wherein said reaction furnace produces a thermal decomposition reaction which precipitates decomposed reaction products of said material gas on the surface of said cladding of said introduced optical fiber, to form an electroconductive hermetic coating;

an eddy current generation and detection sensor arranged near said hermetic coating to generate and detect an eddy current in said hermetic coating;

a high frequency power source for generating a high frequency current which is applied to said eddy current generation and detection sensor and is of a frequency sufficiently high for causing said eddy current generation and detection sensor to generate said eddy current in said hermetic coating;

an average magnetization-intensity changing means for applying said high frequency current from said high frequency power source to said eddy current generation and detection sensor while changing an average magnetization-intensity caused by said high frequency current having a frequency of the current lower than the high frequency of said high frequency current;

means for calculating an electrical resistance of said hermetic coating from said eddy current detected by said eddy current generation and detection sensor; and control means for adjusting at least one hermetic coating forming condition and the adjusting by said control means being based on the electrical resistance from said electrical resistance calculating means.

2. A production apparatus as set forth in claim 1, wherein said adjustment of at least one of said hermetic coating forming condition is adjustment of an amount of said hermetic coating forming material gas introduced to said reaction furnace.

3. A production apparatus as set forth in claim 1, wherein said adjustment of at least one of said hermetic coating forming condition is adjustment of a temperature of at least one of said drawing furnace and said reaction furnace.

4. A production system apparatus as set forth in claim 1, wherein said adjustment of at least one of said hermetic coating forming condition is adjustment of an amount of said hermetic coating forming material gas introduced to said reaction furnace and a hermetic coating forming temperature of at least one of said drawing furnace and said reaction furnace.

5. A production apparatus as set forth in claim 1, wherein said average magnetization-intensity changing means comprises:
- a DC bias power source for generating a DC bias current for biasing said high frequency current;
- an addition circuit for adding said DC bias current to said high frequency current; and
- switching means for alternately enabling transmission of the biased high frequency current from said addition circuit to said eddy current generation and detection sensor, wherein said switching means is responsive to said low frequency.

6. A production apparatus as set forth in claim 1, wherein said average magnetization-intensity changing means comprises:
- a DC bias power source for generating a DC bias current for biasing said high frequency current;
- a low frequency power source for generating an AC current having a predetermined amplitude; and
- an addition circuit for adding the high frequency current from said high frequency power source, the DC bias current from said DC bias power source, and said AC current from said low frequency power source.

7. A production apparatus as set forth in claim 1, wherein said average magnetization-intensity changing means comprises vibration means for changing a distance between said eddy current generation and detection sensor and said hermetic coating and the changing of the distance by said vibration means being responsive to said lower frequency.

8. A production apparatus as set forth in claim 7, wherein said hermetic coating and said eddy current generation and detection sensor having a distance therebetween and said vibration means comprises means for vibrating said eddy current generation and detection sensor with respect to said hermetic coating to change the distance between said hermetic coating and said eddy current generation and detection sensor.

9. A production apparatus as set forth in claim 7, wherein said hermetic coating and said eddy current generation and detection sensor having a distance therebetween and said vibration means comprises means for vibrating said hermetic coating with respect to said eddy current generation and detection sensor to change the distance between said hermetic coating and said eddy current generation and detection sensor.

10. A production apparatus as set forth in claim 1, wherein said means for calculating the electrical resistance has a computer.

11. A production apparatus as set forth in claim 1, further comprising means for forming a protective coating on an outer surface of said hermetic coating.

* * * * *